US007238818B2

(12) United States Patent
Ewen et al.

(10) Patent No.: US 7,238,818 B2
(45) Date of Patent: *Jul. 3, 2007

(54) HETEROCYCLIC METALLOCENES AND POLYMERIZATION CATALYSTS

(75) Inventors: John A. Ewen, Houston, TX (US); Michael J. Elder, Elkton, MA (US); Robert L. Jones, Jr., Elkton, MA (US); Yuri A. Dubitsky, Milan (IT)

(73) Assignee: Basell Polyolefine GmbH, Wesseling (DE)

( * ) Notice: Subject to any disclaimer, the term of this patent is extended or adjusted under 35 U.S.C. 154(b) by 218 days.

This patent is subject to a terminal disclaimer.

(21) Appl. No.: 10/395,686

(22) Filed: Mar. 24, 2003

(65) Prior Publication Data

US 2005/0192418 A1 Sep. 1, 2005

(51) Int. Cl.
*C07F 17/00* (2006.01)
*C08F 7/00* (2006.01)

(52) U.S. Cl. ............... 556/11; 556/12; 556/21; 556/28; 556/30; 556/43; 556/53; 556/56; 556/70; 556/87; 556/408; 534/11; 534/15; 549/3; 549/32; 502/103; 502/117; 526/128; 526/149; 526/150; 526/348.1; 526/348.5; 526/351; 526/352

(58) Field of Classification Search ............ 556/11, 556/12, 21, 28, 30, 43, 53, 56, 70, 87, 406; 534/11, 15; 549/3, 32; 502/103, 117; 526/160, 526/943, 128, 149, 150, 348.1, 348.5, 351, 526/352

See application file for complete search history.

(56) References Cited

U.S. PATENT DOCUMENTS

| 4,287,328 A | 9/1981 | Kikuta et al. |
| 4,316,966 A | 2/1982 | Mineshima et al. |
| 4,530,914 A | 7/1985 | Ewen et al. |
| 4,794,096 A | 12/1988 | Ewen |
| 4,892,851 A | 1/1990 | Ewen et al. |
| 4,935,474 A | 6/1990 | Ewen et al. |
| 4,975,403 A | 12/1990 | Ewen |
| 5,036,034 A | 7/1991 | Ewen |
| 5,122,583 A | 6/1992 | Ewen et al. |
| 5,155,080 A | 10/1992 | Elder et al. |
| 5,225,500 A | 7/1993 | Elder et al. |
| 5,324,800 A | 6/1994 | Welborn, Jr. et al. |
| 5,350,723 A | 9/1994 | Neithamer et al. |
| 5,399,635 A | 3/1995 | Neithamer et al. |
| 5,453,410 A | 9/1995 | Kolthammer et al. |
| 5,459,117 A | 10/1995 | Ewen |
| 5,840,947 A * | 11/1998 | Kuber et al. .............. 556/8 |
| 6,069,237 A * | 5/2000 | Ewen et al. .............. 534/15 |

FOREIGN PATENT DOCUMENTS

| EP | 0 035 242 A1 | 9/1981 |
| EP | 0 277 004 A1 | 8/1988 |
| EP | 0 427 638 A2 | 5/1991 |
| EP | 0 427 697 A2 | 5/1991 |
| EP | 0 537 130 A1 | 4/1993 |

OTHER PUBLICATIONS

Thoma, et al. "Indenyl and Fluorenyl Transition Metal Complexes. IV*. Reactions of 2-and 4-Fluorenes ** With Chromium Hexacarbonyl," *Journal of Organometallic Chemistry*, vol. 192, pp. 359-365 (1980).

Thoma, et al. "Indenyl and Fluorenyl Transition Metal Complexes. VIII*. Synthesis, Structure and Properties of Metal Carbonyl Derivatives of Azafluorenes, Indole, Carbazole And The Corresponding Anions," *Journal of Organometallic Chemistry*, vol. 231, pp. 5-24 (1982).

Ustynyuk et al., "Idenyl and Fluorenyl Transitional Metal Complexes," *JOMC*, vol. 231, pp. 5-24 (1982).

Tani et al., "Transition Metal Complexes of I,1'- Bis(2-prydyl)ferrocene", *Chemistry Letters*, pp. 2407-2050 (1991).

Resconi et al., "High-Molecular-Weight Atactic Polypropylene from Metallocene Catalysts", *Organometallics*, vol. 15, No. 3, pp. 998-1005 (1991).

\* cited by examiner

*Primary Examiner*—Robert D. Harlan
(74) *Attorney, Agent, or Firm*—Bryan Cave LLP; Warren MacRae, Esq.

(57) ABSTRACT

A new class of heterocyclic metallocenes, a catalytic system containing them and a process for polymerizing addition polymerizable monomers using said catalytic system are disclosed; the heterocyclic metallocenes correspond to the formula (I): $Y_j R''_i Z_{jj} MeQ_k P_l$ wherein Y is a coordinating group containing a six π electron central radical directly coordinating Me, to which are associated one or more radicals containing at least one non-carbon atom selected from B, N, O, Al, Si, P, S, Ga, Ge, As, Se, In, Sn, Sb and Te; R" is a divalent bridge between the Y and Z groups; Z is a coordinating group, optionally being equal to Y; Me is a transition metal; Q is halogen or hydrocarbon substituents; P is a counterion; i is 0 or 1; j is 1–3; jj is 0–2; k is 1–3; and l is 0–2.

38 Claims, No Drawings

HETEROCYCLIC METALLOCENES AND POLYMERIZATION CATALYSTS

FIELD OF THE INVENTION

The present invention relates to new heterocyclic metallocenes and to catalytic systems for the production of homopolymers and copolymers having a wide range of properties, including linear low density, high density, atactic, isotactic and syndiotactic polymers.

More particularly, this invention relates to a new class of metallocenes containing at least one heteroatom in a ring system associated with a six $\pi$ electron central radical directly coordinating a transition metal, said metallocene being capable of polymerizing addition polymerizable monomers.

BACKGROUND OF THE INVENTION

Polymerization of vinyl monomers, both mono-olefins and conjugated dienes, has focused on transition metal catalysts since the work of Ziegler and Natta. These catalysts are based on a central transition metal ion or atom surrounded by a set of coordinating ligands and modified by various cocatalysts.

By controlling the nature of the ligand system, the central transition metal ion or atom, and the co-catalyst, highly active catalytic agents can be made. In addition, catalysts can be made that yield polymers with high degrees of addition regularity, and in the case of non-ethylene type monomers, stereoregular or tactioselective and/or tactiospecific polymers can be made.

U.S. Pat. No. 3,051,690 discloses a process of polymerizing olefins to controlled high molecular weight polymers by the controlled addition of hydrogen to a polymerization system that includes a hydrocarbon insoluble reaction product of a Group IVB, VB, VIB and VIII compound and an alkali metal, alkaline earth metal, zinc, earth metal or rare earth metal organometallic compound. It is further known that certain metallocenes, such as bis(cyclopentadienyl) titanium or zirconium dialkyls, in combination with aluminum alkyl/water cocatalysts, form homogeneous catalyst systems for the polymerization of ethylene.

German Patent Application 2,608,863 discloses the use of a catalyst system for the polymerization of ethylene, consisting of bis(cyclopentadienyl) titanium dialkyl, aluminum trialkyl and water. Furthermore, German Patent Application 2,608,933 discloses an ethylene polymerization catalyst system including a catalyst of general formula $(Cp)_n ZrY_{4-n}$, where n is a number from 1 to 4 and Y is a hydrocarbon group or a metalloalkyl in combination with an aluminum trialkyl cocatalyst and water (Cp indicates cyclopentadienyl).

European Patent Appl. No. 0035242 discloses a process for preparing ethylene and atactic propylene polymers in the presence of a halogen-free Ziegler catalyst system of general formula $(Cp)_n MeY_{4-n}$, where n is an integer from 1 to 4, Me is a transition metal, especially zirconium, and Y is either hydrogen, a $C_1$–$C_5$ alkyl, a metalloalkyl group or other radical, in combination with an alumoxane.

U.S. Pat. No. 5,324,800 discloses a catalyst system for polymerizing olefins including a metallocene catalyst of general formula $(C_5R'_m)_p R''_s (C_5R'_m) MeQ_{3-p}$ or $R''_s (C_5R'_m)_2 MeQ'$, where $(C_5R'_m)$ is a substituted Cp group, and an alumoxane.

Polyolefins can be prepared in a variety of configurations that correspond to the manner in which each new monomer unit is added to a growing polyolefin chain. For non-ethylene-polyolefins four basic configurations are commonly recognized, i.e. atactic, hemi-isotactic, isotactic and syndiotactic.

A given polymer may incorporate regions of each configurational type, not exhibiting the pure or nearly pure configuration.

On the opposite polymers of monomers symmetrically equivalent to ethylene (i.e., the 1,1 substituents are identical and the 2,2 substituents are identical, sometimes referred to as "ethylene-like monomers") can have no tacticity.

Atactic polymers exhibit no regular order of repeat unit orientation in the polymer chain, i.e. the substituents are not regularly ordered relative to a hypothetical plane containing the polymer backbone (the plane is oriented such that the substituents on the pseudo-asymmetric carbon atoms are either above or below the plane). Instead, atactic polymers exhibit a random distribution of substituent orientations.

Additionally, other type of catalyst belonging to the family of metallocene catalyst are the so-called "constrained geometry catalysts", where one of the cyclopentadienyl groups has been replaced by a heteroatom ligand, such as an amino or phosphino anion. Such catalysts are described in U.S. Pat. Nos.: 5,453,410, 5,399,635, and 5,350,723.

Besides metallocene catalyst that produce polyethylene and atactic polyolefins, certain metallocenes are also known to produce polymers with varying degrees of stereoregularity or tactiospecificity, such as isotactic, syndiotactic, and hemi-isotactic polymers, which have unique and regularly repeating stereochemistries or substituent orientations relative to the plane containing the polymer backbone.

Isotactic polymers have the substituents attached to the asymmetric carbon atoms oriented on the same side, relative to the polymer backbone, i.e. the substituents are all either configured above or below the plane containing the polymer backbone. Isotacticity can be determined through the use of NMR. In conventional-NMR nomenclature, an isotactic pentad is represented by "mmmm" where each "m" represents a "meso" dyad or successive monomer units having the substituents oriented on the same side relative to the polymer backbone. As is well known in the art, any inversion of a pseudo-asymmetric carbon in the chain lowers the degree of isotacticity and crystallinity of the polymer.

In contrast, the syndiotactic structure is typically described as having the substituents attached to the asymmetric carbon atoms, disposed pseudo-enantiomorphically, i.e., the substituents are oriented alternately and regularly above and below the plane containing the polymer chain. Syndiotacticity can also be determined through the use of NMR. In NMR nomenclature, a syndiotactic pentad is represented by "rrrr", wherein each "r" represents a "racemic" dyad, i.e. successive substituents on alternate sides of the plane. The percentage of "r" dyads in the chain determines the degree of syndiotacticity of the polymer.

There are other variations in polymer structures as well. For instance, hemi-isotactic polymers are ones in which every other pseudo-asymmetric carbon atom has its substituent oriented on the same side relative to the plane containing the polymer backbone. While, the other pseudo-asymmetric carbon atoms can have their substituents oriented randomly, either above or below the plane. Since only every other pseudo-asymmetric carbon is in an isotactic configuration, the term hemi is applied.

Isotactic and syndiotactic polymers are crystalline polymers and are insoluble in cold xylene. Crystallinity distinguishes both syndiotactic and isotactic polymers from hemi-isotactic and atactic polymers, that are soluble in cold xylene and are non-crystalline. While it is possible for a catalyst to produce all four types of polymers (atactic, hemi-isotactic, isotactic and syndiotactic), it is desirable for a catalyst to produce predominantly or essentially isotactic or syndiotactic polymers having very little atactic contents and few stereochemical defects.

Several catalysts that produce isotactic polyolefins are disclosed in U.S. Pat. Nos. 4,794,096 and 4,975,403, as well as European Pat. Appl. 0,537,130. Several catalysts that produce syndiotactic polyolefins are disclosed in U.S. Pat. Nos. 3,258,455, 3,305,538; 3,364,190, 4,852,851, 5,155,080, 5,225,500, and 5,459,117.

Besides neutral metallocenes, cationic metallocenes are known to result in polymers with varying degrees of tactiospecificity. Cationic metallocene catalysts are disclosed in European Patent Applications 277,003 and 277,004. Catalysts that produce hemi-isotactic polyolefins are disclosed in U.S. Pat. No. 5,036,034.

In addition to homopolymers of monoolefins, polymerization catalysts for preparing copolymers of monoolefins, or polymers of di-functional olefins, or copolymers of di-functional olefins and monoolefins can be prepared using coordinated metal catalysts, including metallocene catalysts.

Although many metallocene catalysts are now available, the need for new ligand systems and new metallocene catalysts or catalyst precursors for the polymerization of olefins is still important and would represent a significant advancement in the art. Such new ligand systems and the catalysts derived therefrom can offer new design approaches for making highly-stereoregular or tactiospecific polymers essentially free of defects, polymers with controlled defect statistics, and copolymers with controlled properties, or new approaches for molecular weight control and for the control of other polymer properties.

SUMMARY OF THE INVENTION

The present invention provides a new class of heterocyclic metallocenes for the polymerization of olefins useful to prepare polymer products with desired properties, such as a given molecular weight, molecular weight distribution, density, tacticity and/or terminal unsaturation.

The metallocenes according to the present invention contain at least one heteroatom in a ring system associated with a six π electron central radical directly coordinating a transition metal belonging to Group 3, 4, 5, 6 or to the lanthanide or actinide series of the Periodic Table of the Elements (IUPAC version).

Said metallocenes are useful for the polymerization of addition polymerizable monomers, such as α-olefins, into homopolymers and/or copolymers.

The metallocenes of the present invention comprise organometallic coordination compounds of mono, di or tri-functional ligand systems coordinated to transition metal complexes, preferably complexes of an element of Group 3, 4, or 5 or of the lanthanide series of elements from the Periodic Table, where the ligand system includes at least one six π electron central radical to which are associated one or more radicals containing at least one heteroatom.

The metallocenes of the present invention correspond to formula (I):

wherein
(1) Y is a coordinating group containing a six π electron central radical directly coordinating Me, to which are associated one or more radicals containing at least one non-carbon atom selected from B, N, O, Al, Si, P, S, Ga, Ge, As, Se, In, Sn, Sb and Te;
(2) R" is a divalent bridge between the Y and Z groups;
(3) Z is a coordinating group having the same meanings as Y or is an open pentadienyl containing group, a cyclopentadienyl containing group, a heterocyclic cyclopentadienyl containing group, a nitrogen containing group, a phosphorous containing group, an oxygen containing group or a sulfur containing group;
(4) Me is an element belonging to Group 3, 4, 5, 6 or to the lanthanide or actinide series of the Periodic Table of Elements;
(5) Q is a linear or branched, saturated or unsaturated alkyl radical, aryl radical, alkylaryl radical, arylalkyl radical or a halogen atom;
(6) P is a stable non-coordinating or pseudo non-coordinating counterion;
(7) i is an integer having a value of 0 or 1;
(8) j is an integer having a value from 1 to 3;
(9) jj is an integer having a value from 0 to 2;
(10) k is an integer having a value from 1 to 3; and
(11) l is an integer having a value from 0 to 2.

Moreover, formula (I) also describes cationic metallocenes where l=1 or 2. Said cationic metallocenes can be prepared by reacting an ion-pair or a strong Lewis acid compound with a neutral metallocene (i.e., l=0) to form a cationic metallocene, either prior to or concurrent with contacting the neutral metallocene with monomer. Cationic metallocenes are used analogously to neutral ones to polymerize addiction polymerizable monomers.

Another object of the present invention is a class of ligands of formula (II):

wherein Y, R", Z, j, i and jj have the meanings reported above; said ligands are useful as intermediates in the preparation of the heterocyclic metallocenes of the present invention.

Another object of the present invention is a catalytic system for the polymerization of addition polymerisable monomers, comprising the reaction product between:
an heterocyclic metallocene of formula (I) and
a suitable co-catalyst.

The present invention further provides a process for polymerizing addition polymerizable monomers comprising contacting at least one of the above catalytic systems with at least one addition polymerizable monomer. Preferably, the metallocene and the monomer are contacted together in a reaction zone. Alternatively, the metallocenes of formula (I) can be combined with a co-catalyst, such as an alkyl aluminum or an alumoxane, either prior to or after the metallocene of formula (I) is brought into contact with monomer.

Furthermore, the metallocenes of formula (I) may be used for pre-polymerization before polymerisation with bulk monomer and/or prior to the stabilization of the reaction conditions.

The present invention can also be practiced to produce intimate blends of different types of polymers by contacting a metallocene of formula (I) designed for each different polymer type with one or more monomers.

The preferred applications of practicing this invention is in the production of polyethylene, polyethylene copolymers, isotactic, syndiotactic, hemi-isotactic or atactic polypropylene, or mixtures thereof, polypropylene copolymers, as well as polymers and copolymers of other addition polymerizable monomers.

The present invention further includes methods for preparing metallocenes of formula (I) and their ligands, and methods for activating the metallocenes of formula (I) where l=0 into catalytically active polymerization agents.

DETAILED DESCRIPTION OF THE INVENTION

In the present detailed description the following definitions are used:

"Central Radical" means a six π electron radical directly coordinating the transition metal, such as the five member bring in cyclopentadiene, indene or fluorene;

"HCy" means a ligand including a central six π electron radical having an associated radical containing at least one heteroatom;

"Cp" means a cyclopentadienyl ring;

"HCp" means a Cp ring containing one or more heteroatoms;

"Op" means an open pentadienyl ligand having five atoms in an all cis configuration and having six π electrons delocalized over the five atoms;

The "h-" prefix will be used to connote the heterocyclic analogs of aromatic ring systems containing a central five membered ring and a heterocyclic fused ring, e.g. h-Ind for an indene or indane ring system containing at least one heteroatom in the six membered ring of the fused ring system, h-Flu for a fluorene or fluorane ring system containing at least one heteroatom in one or both of the six membered rings of the fused ring system, or h-Pta for a pentalene or pentalane ring system containing a least one heteroatom in only one of the fused five membered rings of the pentalene ring system; and "o-" prefix will be used to connote the open-pentadienyl analog of above described fused ring systems The Applicant found a new class of heterocyclic metallocenes with wide application for the production of polymers of addition polymerizable monomers; said metallocenes present two to three coordinating ligands, where at least one of said coordinating ligands has a central six π electron radical directly coordinated to a suitable transition metal, to which is associated a group containing at least one heteroatom (sometimes abbreviated "HCy" group). The electrons in the HCy group can be delocalized over the entire groups.

The present invention is directed towards metallocenes and catalytic systems containing them useful in the polymerization of addition polymerizable monomers. In particular, the present invention is directed towards metallocenes and catalytic systems for the polymerization of polymerizable vinyl monomers, including α-olefins (such as ethylene, propylene and butylene) to produce polymers such as linear low density polyethylene (LLDPE), high density polyethylene (HDPE) and polypropylene (isotactic, syndiotactic, hemi-isotactic, atactic or mixtures thereof). The resulting polymers are intended for fabrication into articles by extrusion, injection molding, thermoforming, rotational molding, or other techniques known in the state of the art.

The polymers which can be prepared using the metallocenes of this invention include homopolymers and copolymers of vinyl monomers, having from 2 to 20 carbon atoms, and preferably from 2 to 12 carbon atoms; said vinyl monomers are preferably ethylene, propylene, butylene and styrene. In addition, said vinyl monomers can also include various heteroatoms, such as acrylonitrile and vinyl pyridine.

The heterocyclic metallocenes of this invention contain one or more mono-, bi- and/or tri-functional ligands coordinated to, complexed with, or otherwise associated with a suitable transition metal, where at least one of said ligands is a HCy ligand coordinating the transition metal.

Particularly preferred heterocyclic metallocenes of the present invention include those represented by formula (I):

$$Y_j R''_i Z_{jj} MeQ_k P_l \qquad (I)$$

where:

(1) Y is a coordinating ligand comprising a six π electron central radical, directly coordinating Me, to which is associated a group containing at least one non-carbon atom selected from B, N, O, Al, Si, P, S, Ga, Ge, As, Se, In, Sn, Sb and Te;

(2) R" is a divalent bridge linking Y and Z and can be a linear or branched $C_1$–$C_{20}$ alkenyl radical, a $C_3$–$C_{12}$ bicyclic radical, an aryl radical or a diaryl allyl radical, said radicals optionally containing silicon, germanium, phosphorous, nitrogen, boron or aluminum atoms;

(3) Z is a coordinating group having the same meanings as Y or is an open pentadienyl containing group, a cyclopentadienyl containing group, a heterocyclic cyclopentadienyl containing group, a nitrogen containing group, a phosphorous containing group, an oxygen containing group or a sulfur containing group;

(4) Me is an element belonging to Group 3, 4, or 5 or to the lanthanide series, preferably Lu, La, Nd, Sm, or Gd;

(5) Q is a linear or branched, saturated or unsaturated alkyl radical, aryl radical, alkylaryl radical, arylalkyl radical or a halogen atom;

(6) P is a stable non-coordinating or pseudo non-coordinating counterion;

(7) i is an integer having a value of 0 or 1;

(8) j is an integer having a value from 1 to 3;

(9) jj is an integer having a value from 0 to 2;

(10) k is an integer having a value from 1 to 3; and

(11) l is an integer having a value from 0 to 2.

A particularly important subclass of the metallocenes of this invention are represented by formula (III):

$$YR''ZMeQ_k P_l \qquad (III)$$

where Y is a HCy group and Z is a non-HCy group and where R", Me, Q, P, k, and l are as described above (i=1, j=1 and jj=1 in formula (I)) and YR"Z is a ligand of the invention.

Non limiting examples of said metallocenes are:

isopropylidene(cyclopentadienyl)(7-cyclopentadithiophene)zirconium dichloride;

dimethylsilanediyl(cyclopentadienyl)(7-cyclopentadithiophene)zirconium dichloride;

isopropylidene(3-methylcyclopentadienyl)(7-cyclopentadithiophene)zirconium dichloride;

dimethylsilanediyl(3-methylcyclopentadienyl)(7-cyclopentadithiophene)zirconium dichloride;

isopropylidene(3-ethylcyclopentadienyl)(7-cyclopentadithiophene)zirconium dichloride;

dimethylsilanediyl(3-ethylcyclopentadienyl)(7-cyclopentadithiophene)zirconium dichloride;

isopropylidene(3-i-propylcyclopentadienyl)(7-cyclopentadithiophene)zirconium dichloride;

dimethylsilanediyl(3-i-propylcyclopentadienyl)(7-cyclopentadithiophene)zirconium dichloride;

isopropylidene(3-n-butylcyclopentadienyl)(7-cyclopentadithiophene)zirconium dichloride;
dimethylsilanediyl(3-n-butylcyclopentadienyl)(7-cyclopentadithiophene)zirconium dichloride;
isopropylidene(3-t-butylcyclopentadienyl)(7-cyclopentadithiophene)zirconium dichloride;
dimethylsilanediyl(3-t-butylcyclopentadienyl)(7-cyclopentadithiophene)zirconium dichloride;
isopropylidene(3-trimethylsilylcyclopentadienyl)(7-cyclopentadithiophene)zirconium dichloride;
dimethylsilanediyl(3-trimethylsilylcyclopentadienyl)(7-cyclopentadithiophene)zirconium dichloride;
isopropylidene(cyclopentadienyl)(7-cyclopentadipyrrole)zirconium dichloride;
dimethylsilanediyl(cyclopentadienyl)(7-cyclopentadipyrrole)zirconium dichloride;
isopropylidene(3-methylcyclopentadienyl)(7-cyclopentadipyrrole)zirconium dichloride;
dimethylsilanediyl(3-methylcyclopentadienyl)(7-cyclopentadipyrrole)zirconium dichloride;
isopropylidene(3-ethylcyclopentadienyl)(7-cyclopentadipyrrole)zirconium dichloride;
dimethylsilanediyl(3-ethylcyclopentadienyl)(7-cyclopentadipyrrole)zirconium dichloride;
isopropylidene(3-i-propylcyclopentadienyl)(7-cyclopentadipyrrole)zirconium dichloride;
dimethylsilanediyl(3-i-propylcyclopentadienyl)(7-cyclopentadipyrrole)zirconium dichloride;
isopropylidene(3-t-butylcyclopentadienyl)(7-cyclopentadipyrrole)zirconium dichloride;
dimethylsilanediyl(3-t-butylcyclopentadienyl)(7-cyclopentadipyrrole)zirconium dichloride;
isopropylidene(cyclopentadienyl)(7-cyclopentadiphosphole)zirconium dichloride;
dimethylsilanediyl(cyclopentadienyl)(7-cyclopentadiphosphole)zirconium dichloride;
isopropylidene(3-methylcyclopentadienyl)(7-cyclopentadiphosphole)zirconium dichloride;
dimethylsilanediyl(3-methylcyclopentadienyl)(7-cyclopentadiphosphole)zirconium dichloride;
isopropylidene(3-ethylcyclopentadienyl)(7-cyclopentadiphosphole)zirconium dichloride;
dimethylsilanediyl(3-ethylcyclopentadienyl)(7-cyclopentadiphosphole)zirconium dichloride;
isopropylidene(3-i-propylcyclopentadienyl)(7-cyclopentadiphosphole)zirconium dichloride;
dimethylsilanediyl(3-i-propylcyclopentadienyl)(7-cyclopentadiphosphole)zirconium dichloride;
isopropylidene(3-t-butylcyclopentadienyl)(7-cyclopentadiphosphole)zirconium dichloride;
dimethylsilanediyl(3-t-butylcyclopentadienyl)(7-cyclopentadiphosphole)zirconium dichloride;
isopropylidene(2-methylthiapentalene)(2-methylindene)zirconiumdichloride;
dimethylsilanediyl(2-methylthiapentalene)(2-methylindene)zirconiumdichloride;
isopropylidene(2-ethylthiapentalene)(2-ethylindene)zirconiumdichloride;
dimethylsilanediyl(2-ethylthiapentalene)(2-ethylindene)zirconiumdichloride;
isopropylidene(2-i-propylthiapentalene)(2-i-propylindene)zirconiumdichloride;
dimethylsilanediyl(2-i-propylthiapentalene)(2-i-propylindene)zirconiumdichloride;
isopropylidene(2-t-butylthiapentalene)(2-t-butylindene)zirconiumdichloride;
dimethylsilanediyl(2-t-butylthiapentalene)(2-t-butylindene)zirconiumdichloride;
isopropylidene(2-trimethylsilylthiapentalene)(2-trimethylsilylindene)zirconium dichloride;
dimethylsilanediyl(2-trimethylsilylthiapentalene)(2-trimethylsilylindene)zirconium dichloride;
isopropylidene(cyclopentadienyl)(thiapentalene)zirconium dichloride;
dimethylsilanediyl(cyclopentadienyl)(thiapentalene)zirconium dichloride;
isopropylidene(indenyl)(thiapentalene)zirconium dichloride;
dimethylsilanediyl(indenyl)(thiapentalene)zirconium dichloride;
isopropylidene(fluorenyl)(thiapentalene)zirconium dichloride;
dimethylsilanediyl(fluorenyl)(thiapentalene)zirconium dichloride;
isopropylidene(cyclopentadienyl)(2-methylthiapentalene)zirconium dichloride;
dimethylsilanediyl(cyclopentadienyl)(2-methylthiapentalene)zirconium dichloride;
phenylmethylsilanediyl(cyclopentadienyl)(2-methylthiapentalene)zirconium dichloride;
isopropylidene(cyclopentadienyl)(2-ethylthiapentalene)zirconium dichloride;
dimethylsilanediyl(cyclopentadienyl)(2-ethylthiapentalene)zirconium dichloride;
isopropylidene(cyclopentadienyl)(2-n-butylthiapentalene)zirconium dichloride;
dimethylsilanediyl(cyclopentadienyl)(2-n-buthylthiapentalene)zirconium dichloride;
isopropylidene(cyclopentadienyl)(2-i-propylthiapentalene)zirconium dichloride;
dimethylsilanediyl(cyclopentadienyl)(2-i-propylthiapentalene)zirconium dichloride;
isopropylidene(cyclopentadienyl)(2-phenylthiapentalene)zirconium dichloride;
dimethylsilanediyl(cyclopentadienyl)(2-phenylthiapentalene)zirconium dichloride;
isopropylidene(cyclopentadienyl)(2-naphthylthiapentalene)zirconium dichloride;
dimethylsilanediyl(cyclopentadienyl) (2-naphthylthiapentalene)zirconium dichloride;
isopropylidene(cyclopentadienyl)(2-trimethylsilylthiapentalene)zirconium dichloride;
dimethylsilanediyl(cyclopentadienyl)(2-trimethylsilylthiapentalene)zirconium dichloride;
1,2-ethandiylbis(cyclopentadienyl)(2-methylthiapentalene)zirconium dichloride;
isopropylidene(3-methylcyclopentadienyl)(2-methylthiapentalene)zirconium dichloride;
dimethylsilanediyl(3-methylcyclopentadienyl)(2-methylthiapentalene)zirconium dichloride;
isopropylidene(3-ethylcyclopentadienyl)(2-methylthiapentalene)zirconium dichloride;
dimethylsilanediyl(3-ethylcyclopentadienyl)(2-methylthiapentalene)zirconium dichloride;
isopropylidene(3-i-propylcyclopentadienyl)(2-methylthiapentalene)zirconium dichloride;
dimethylsilanediyl(3-i-propylcyclopentadienyl)(2-methylthiapentalene)zirconium dichloride;
isopropylidene(3-n-butylcyclopentadienyl)(2-methylthiapentalene)zirconium dichloride;
dimethylsilanediyl(3-n-butylylcyclopentadienyl)(2-methylthiapentalene)zirconium dichloride;

isopropylidene(3-t-butylcyclopentadienyl)(2-methylthiapentalene)zirconium dichloride;
dimethylsilanediyl(3-t-butylylcyclopentadienyl)(2-methylthiapentalene)zirconium dichloride;
isopropylidene(3-t-butylcyclopentadienyl)(7-cyclopenta[1.2]thiophene[1.4]cyclopentadiene)zirconium dichloride;
dimethylsilanediyl(3-t-butylylcyclopentadienyl)(7-cyclopenta[1.2]thiophene[1.4]cyclopentadiene)zirconium dichloride;
dimethylstanyl(3-t-butylylcyclopentadienyl)(7-cyclopenta[1.2]thiophene[1.4]cyclopentadiene)zirconium dichloride;
isopropylidene(3-t-butylcyclopentadienyl)(7-cyclopenta[1.2]thiophene[1.4]cyclopentadiene)zirconium dichloride;
dimethylsilanediyl(3-t-butylylcyclopentadienyl)(7-cyclopenta[1.2]thiophene[1.4]cyclopentadiene)zirconium dichloride;
isopropylidene(cyclopentadienyl)(azapentalene)zirconium dichloride;
dimethylsilanediyl(cyclopentadienyl)(azapentalene)zirconium dichloride;
isopropylidene(cyclopentadienyl)(2-methyltazapentalenyl)zirconium dichloride;
dimethylsilanediyl(cyclopentadienyl)(2-methylazapentalene)zirconium dichloride;
phenylmethylsilanediyl(cyclopentadienyl)(2-methylazapentalene)zirconium dichloride;
isopropylidene(cyclopentadienyl)(2-ethylazapentalene)zirconium dichloride;
dimethylsilanediyl(cyclopentadienyl)(2-ethylazapentalene)zirconium dichloride;
isopropylidene(cyclopentadienyl)(2-n-butylazapentalene)zirconium dichloride;
dimethylsilanediyl(cyclopentadienyl)(2-n-buthylazapentalene)zirconium dichloride;
isopropylidene(cyclopentadienyl)(2-i-propylazapentalene)zirconium dichloride;
dimethylsilanediyl(cyclopentadienyl)(2-i-propylazapentalene)zirconium dichloride;
isopropylidene(cyclopentadienyl)(2-phenylazapentalene)zirconium dichloride;
dimethylsilanediyl(cyclopentadienyl)(2-phenylazapentalene)zirconium dichloride;
isopropylidene(cyclopentadienyl)(2-naphthylazapentalene)zirconium dichloride;
dimethylsilanediyl(cyclopentadienyl)(2-naphthylazapentalene)zirconium dichloride;
isopropylidene(cyclopentadienyl)(2-trimethylsilylazapentalene)zirconium dichloride;
dimethylsilanediyl(cyclopentadienyl)(2-trimethylsilylazapentalene)zirconium dichloride;
1,2-ethandiylbis(cyclopentadienyl)(2-methylazapentalene)zirconium dichloride;
isopropylidene(3-methylcyclopentadienyl)(2-methylazapentalene)zirconium dichloride;
dimethylsilanediyl(3-methylcyclopentadienyl)(2-methylazapentalene)zirconium dichloride;
isopropylidene(3-ethylcyclopentadienyl)(2-methylazapentalene)zirconium dichloride;
dimethylsilanediyl(3-ethylcyclopentadienyl)(2-methylazapentalene)zirconium dichloride;
isopropylidene(3-i-propylcyclopentadienyl)(2-methylazapentalene)zirconium dichloride;
dimethylsilanediyl(3-i-propylcyclopentadienyl)(2-methylazapentalene)zirconium dichloride;
isopropylidene(3-n-butylcyclopentadienyl)(2-methylazapentalene)zirconium dichloride;
dimethylsilanediyl(3-n-butylylcyclopentadienyl)(2-methylazapentalene)zirconium dichloride;
isopropylidene(3-t-butylcyclopentadienyl)(2-methylazapentalene)zirconium dichloride;
dimethylsilanediyl(3-t-butylylcyclopentadienyl)(2-methylazapentalene)zirconium dichloride;
isopropylidene(3-t-butylcyclopentadienyl)(7-cyclopenta[1.2]pyrrole[1.4]cyclopentadiene)zirconium dichloride;
dimethylsilanediyl(3-t-butylylcyclopentadienyl)(7-cyclopenta[1.2]pyrrole[1.4]cyclopentadiene)zirconium dichloride;
dimethylstanyl(3-t-butylylcyclopentadienyl)(7-cyclopenta[1.2]pyrrole[1.4]cyclopentadiene)zirconium dichloride;
isopropylidene(cyclopentadienyl)(oxapentalene)zirconium dichloride;
dimethylsilanediyl(cyclopentadienyl)(oxapentalene)zirconium dichloride;
isopropylidene(cyclopentadienyl)(borapentalene) zirconium dichloride;
dimethylsilanediyl(cyclopentadienyl)(borapentalene)zirconium dichloride;
isopropylidene(cyclopentadienyl)(phosphapentalene) zirconium dichloride;
dimethylsilanediyl(cyclopentadienyl)(phosphapentalene) zirconium dichloride.

Another important subclass of metallocenes according to the present invention are represented by the formula (IV):

$$YR''YMeQ_kP_l \quad (IV)$$

wherein the Y groups, same or different from each other, are HCy and where R'', Me, Q, P, k, and l are as described above (i=1, j=2 and jj=0 in formula (I)) and YR''Y is a ligand of the invention.

Non limiting examples of these metallocenes are:
isopropylidene(2-methylthiapentalene)zirconiumdichloride;
dimethylsilandiylbis(2-methylthiapentalene)zirconiumdichloride;
isopropylidene(2-ethylthiapentalene) zirconiumdichloride;
dimethylsilandiylbis(2-ethylthiapentalene) zirconiumdichloride;
isopropylidene(2-i-propylthiapentalene) zirconiumdichloride;
dimethylsilandiylbis(2-i-propylthiapentalene) zirconiumdichloride;
isopropylidene(2-t-butylthiapentalene) zirconiumdichloride;
dimethylsilandiylbis(2-t-butylthiapentalene) zirconiumdichloride;
isopropylidene(2-trimethylsilylthiapentalene) zirconiumdichloride;
dimethylsilandiylbis(2-trimethylsilylthiapentalene) zirconiumdichloride;
isopropylidene(2-i-phenylthiapentalene) zirconiumdichloride;
dimethylsilandiylbis(2-i-phenylthiapentalene) zirconiumdichloride;
isopropylidenebis(1-phenyl-2,5-dimethyl-1-azapentalene-4-yl)zirconium dichloride;
dimethylsilandiylbis(1-phenyl-2,5-dimethyl-1-azapentalene-4-yl)zirconium dichloride;
isopropylidenebis(1-phenyl-2,5-diethyl-1-azapentalene-4-yl)zirconium dichloride;
dimethylsilandiylbis(1-phenyl-2,5-diethyl-1-azapentalene-4-yl)zirconium dichloride;

isopropylidenebis(1-phenyl-2,5-di-t-butyl-1-azapentalene-4-yl)zirconium dichloride;
dimethylsilandiylbis(1-phenyl-2,5-di-t-butyl-1-azapentalene-4-yl)zirconium dichloride;
isopropylidenebis(1-phenyl-2,5-di-n-butyl-1-azapentalene-4-yl)zirconium dichloride;
dimethylsilandiylbis(1-phenyl-2,5-di-n-butyl-1-azapentalene-4-yl)zirconium dichloride;
isopropylidenebis(1-phenyl-2,5-di-trimethylsilyl-1-azapentalene-4-yl)zirconium dichloride;
dimethylsilandiylbis(1-phenyl-2,5-di-trimethylsilyl-1-azapentalene-4-yl)zirconium dichloride;
diphenylsilandiylbis(1-phenyl-2,5-dimethyl-1-azapentalene-4-yl)zirconium dichloride;
methylphenylsilandiylbis(1-phenyl-2,5-di-methyl-1-azapentalene-4-yl)zirconium dichloride;
ethylphenylsilandiylbis(1-phenyl-2,5-dimethyl-1-azapentalene-4-yl)zirconium dichloride;
1,2-ethandiylbis(1-phenyl-2,5-di-methyl-1-azapentalene-4-yl)zirconium dichloride;
isopropylidenebis(1-phenyl-2,5-dimethyl-1-phosphapentalene-4-yl)zirconium dichloride;
dimethylsilandiylbis(1-phenyl-2,5-dimethyl-1-phosphapentalene-4-yl)zirconium dichloride;
isopropylidenebis(1-phenyl-2,5-diethyl-1-phosphapentalene-4-yl)zirconium dichloride;
dimethylsilandiylbis(1-phenyl-2,5-diethyl-1-phosphapentalene-4-yl)zirconium dichloride;
isopropylidenebis(1-phenyl-2,5-di-t-butyl-1-phosphapentalene-4-yl)zirconium dichloride;
dimethylsilandiylbis(1-phenyl-2,5-di-t-butyl-1-phosphapentalene-4-yl)zirconium dichloride;
isopropylidenebis(1-phenyl-2,5-di-n-butyl-1-phosphapentalene-4-yl)zirconium dichloride;
dimethylsilandiylbis(1-phenyl-2,5-di-n-butyl-1-phosphapentalene-4-yl)zirconium dichloride;
isopropylidenebis(1-phenyl-2,5-di-trimethylsilyl-1-phosphapentalene-4-yl)zirconium dichloride;
dimethylsilandiylbis(1-phenyl-2,5-di-trimethylsilyl-1-phosphapentalene-4-yl)zirconium dichloride;
diphenylsilandiylbis(1-phenyl-2,5-dimethyl-1-phosphapentalene-4-yl)zirconium dichloride;
methylphenylsilandiylbis(1-phenyl-2,5-di-methyl-1-phosphapentalene-4-yl)zirconium dichloride;
ethylphenylsilandiylbis(1-phenyl-2,5-dimethyl-1-phosphapentalene-4-yl)zirconium dichloride;
1,2-ethandiylbis(1-phenyl-2,5-di-methyl-1-phosphapentalene-4-yl)zirconium dichloride;
isopropylidenebis(4-phenyl-2,6-dimethyl-1-thiopentalene-3-yl)zirconium dichloride;
dimethylsilandiylbis(4-phenyl-2,6-dimethyl-1-thiopentalene-3-yl)zirconium dichloride;
isopropylidenebis(4-phenyl-2,6-diethyl-1-thiopentalene-3-yl)zirconium dichloride;
dimethylsilandiylbis(4-phenyl-2,6-diethyl-1-thiopentalene-3-yl)zirconium dichloride;
isopropylidenebis(4-phenyl-2,6-di-n-butyl-1-thiopentalene-3-yl)zirconium dichloride;
dimethylsilandiylbis(4-phenyl-2,6-di-n-butyl-1-thiopentalene-3-yl)zirconium dichloride;
isopropylidenebis(4-phenyl-2,6-di-1-propyl-1-thiopentalene-3-yl)zirconium dichloride;
dimethylsilandiylbis(4-phenyl-2,6-di-1-propyl-1-thiopentalene-3-yl)zirconium dichloride;
isopropylidenebis(4-phenyl-2,6-di-(3-pyridyl)-1-thiopentalene-3-yl)zirconium dichloride;
dimethylsilandiylbis(4-phenyl-2,6-di-(3-pyridyl)-1-thiopentalene-3-yl)zirconium dichloride;
isopropylidenebis(4-phenyl-2-methyl-6-(3-pyridyl)-1-thiopentalene-3-yl)zirconium dichloride;
dimethylsilandiylbis(4-phenyl-2-methyl-6-(3-pyridyl)-1-thiopentalene-3-yl)zirconium dichloride;
isopropylidenebis(4-phenyl-2-methyl-6-(3-chinolyl)-1-thiopentalene-3-yl)zirconium dichloride;
dimethylsilandiylbis(4-phenyl-2-methyl-6-(3-chinolyl)-1-thiopentalene-3-yl)zirconium dichloride;
isopropylidenebis(4-phenyl-2,6-di-trimethylsilyl-1-thiopentalene-3-yl)zirconium dichloride;
dimethylsilandiylbis(4-phenyl-2,6-di-trimethylsilyl-1-thiopentalene-3-yl)zirconium dichloride;
1,2-ethandiylbis(4-phenyl-2,6-dimethyl-1-thiopentalene-3-yl)zirconium dichloride;
1,3-propandiylbis(4-phenyl-2,6-dimethyl-1-thiopentalene-3-yl)zirconium dichloride;
isopropylidene(3-methylthiopentalene-4-yl)(1-phenyl-2,5-dimethyl-1-azapentalene-4-yl)zirconium dichloride;
dimethylsilandiyl(3-methylthiopentalene-4-yl)(1-phenyl-2,5-dimethyl-1-azapentalene-4-yl)zirconium dichloride;
isopropylidene(3-methylthiopentalene-4-yl)(1-methyl-2,5-dimethyl-1-azapentalene-4-yl)zirconium dichloride;
dimethylsilandiyl(3-methylthiopentalene-4-yl)(1-methyl-2,5-dimethyl-1-azapentalene-4-yl)zirconium dichloride;
isopropylidene(3-methylthiopentalene-4-yl)(1-t-butyl-2,5-dimethyl-1-azapentalene-4-yl)zirconium dichloride;
dimethylsilandiyl(3-methylthiopentalene-4-yl)(1-t-butyl-2,5-dimethyl-1-azapentalene-4-yl)zirconium dichloride;
isopropylidene(3-methylthiopentalene-4-yl)(1-methyl-2,5-dimethyl-1-phosphapentalene-4-yl)zirconium dichloride;
dimethylsilandiyl(3-methylthiopentalene-4-yl)(1-methyl-2,5-dimethyl-1-phosphapentalene-4-yl)zirconium dichloride;
isopropylidene(3-methylthiopentalene-4-yl)(1-t-butyl-2,5-dimethyl-1-phosphapentalene-4-yl)zirconium dichloride;
dimethylsilandiyl(3-methylthiopentalene-4-yl)(1-t-butyl-2,5-dimethyl-1-phosphapentalene-4-yl)zirconium dichloride;
isopropylidene(3-methylthiopentalene-4-yl)(1-phenyl-2,5-dimethyl-1-phosphapentalene-4-yl)zirconium dichloride;
dimethylsilandiyl(3-methylthiopentalene-4-yl)(1-phenyl-2,5-dimethyl-1-phosphapentalene-4-yl)zirconium dichloride;

Another subclass of metallocenes of the invention is represented by formulae (III) or (IV), wherein i=0 and the remaining variable have the meanings reported above.

Non limiting examples of these metallocenes are:
bis(2-methylthiapentalene)zirconiumdichloride;
bis(2-methylazapentalene)zirconiumdichloride;
bis(2-methylphosphapentalene)zirconiumdichloride;
bis(2-ethylthiapentalene)zirconiumdichloride;
bis(2-ethylazapentalene)zirconiumdichloride;
bis(2-ethylphosphapentalene)zirconiumdichloride;
bis(2-i-propylthiapentalene)zirconiumdichloride;
bis(2-i-propylazapentalene)zirconiumdichloride;
bis(2-i-propylphosphapentalene)zirconiumdichloride;
bis(2-t-butylthiapentalene)zirconiumdichloride;
bis(2-t-butylazapentalene)zirconiumdichloride;
bis(2-t-butylphosphapentalene)zirconiumdichloride.

As used in the description of the metallocenes of formulae (I), (III) and (IV), the term "associated" to a central atom, in the context of the group containing at least one heteroatom, "associated to a central 6 π electron radical, means that said heteroatom is not an endocyclic member of the central six electron radical directly coordinating Me. For example, the heteroatom could be part of a ring condensed to the central six electron radical, such as in thiapentalene, azapentalene, dithiatricyclounnonatetraene, diazatricyclounnonatetraene or in thiaazatricyclounnonatetraene or the heteroatom can be part of a radical linked to the central six electron radical, such as a heterocyclic radical substituent bonded to the central radical (e.g. 3-pyridylCp group).

Yet, another important subclass of metallocenes of this invention are those capable of producing polymers having varying degrees of tacticity. Such metallocenes are generally represented by bridged metallocenes of formulae (III) and/or (IV) (i.e., containing bridged ligands) having specific substitution patterns that are capable of imparting tactioselectivity to the metallocenes during polymerization, resulting in the formation of tactioselective polymers.

Generally, tactioselective catalysts, and even tactiospecific catalysts, are formed when in the metallocenes of formulae (III) and (IV), Y and/or Z groups bear the same or different substituents, in some or all of the positions α and β to the atoms bearing the bridging group R″, such that at least one β substituent is a bulky substituent (i.e. sterically bulkier than hydrogen and preferably sterically bulkier than a methyl group or an aromatic carbon atom, which has essentially the same relative steric size as a methyl group). Preferably, said metallocenes possess a specific overall symmetry. Additional information on the effect of bulky β substituent can be found in U.S. Pat. No. 5,459,117.

Metallocenes of formulae (III), capable of yielding polymers with varying degrees of selectivity to the isotactic joining of monomer units ("isoselective metallocenes"), including nearly isospecific polymers ("isospecific metallocenes"), must show either C2 or pseudo-C2 symmetry. In isoselective metallocenes neither Y nor Z is bilaterally or pseudo-bilaterally symmetric, and both Y and Z have a single bulky β substituent irrespective of the number and type of α-substituents. Alternatively, in isoselective metallocenes Y or Z, but not both, is bilaterally or pseudo-bilaterally symmetric and the non-bilaterally symmetric group has only one bulky β substituent. Analogous isoselective metallocenes can be designed from the metallocenes of formula (IV), but where the substituents are on one or both of the Y ligands.

Metallocenes of formula (III) capable of yielding polymers with varying degrees of selectivity to the syndiotactic joining of monomer units ("syndioselective"), including syndiospecific polymers ("syndiospecific metallocenes"), must show either Cs or pseudo-Cs symmetry. In syndioselective catalysts both Y and Z are bilaterally or pseudo-bilaterally symmetric and either Y or Z, but not both, have bulky β substituents irrespective of the number and type of α-substituents. Analogous syndioselective metallocenes can be designed from the metallocenes of formula (IV), but all substitution will occur on the two Y groups.

In the case of metallocenes of formulae (III) and (IV) having non Cp type groups (i.e. ligands not having six π electrons delocalized over five atoms either in an all cis configuration or in a five membered ring, such as NR⁻, PR⁻, O⁻ or S⁻), the substituents on the non-Cp type group and the substituents on the HCy group must operate to sterically constrain the metallocenes so that the resulting polymer has some degree of tacticity. In the case of oxide or sulfide containing metallocenes where the oxygen or sulfur atom is bridged through the divalent bridge R″ to the HCy ligand, the HCy ligand will impose the control over polymer chain propagation by the existence of one or more substituents.

In a particularly preferred class of metallocenes of the present invention, the Y ligand is a heterocyclic ring fused to the central six π electron central radical. Said class is envisaged by formulae (I), (III) and (IV), wherein Y is a substituted cyclopentadienyl group represented by the following structure:

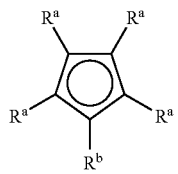

wherein the groups $R^a$, identical or different from each other, are selected from the group consisting of hydrogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, and wherein at least two adjacent $R^a$ groups can form a condensed heterocyclic $C_5$–$C_7$ ring containing at least one non-carbon atom selected from B, N, O, Al, Si, P, S, Ga, Ge, As, Se, In, Sn, Sb and Te;

$R^b$ is hydrogen, halogen, linear or branched, saturated or unsaturated, $C_1$–$C_{20}$-alkyl, $C_1$–$C_{20}$-alkoxyl, $C_6$–$C_{20}$-aryl, $C_7$–$C_{20}$-alkylaryl, $C_7$–$C_{20}$-arylalkyl $C_1$–$C_{20}$ acyloxyl group, optionally containing a silicon atom, or $R^b$ is a bridging divalent group R″ as defined above.

The preferred Y groups are represented by the following formulae:

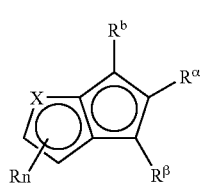
(a)

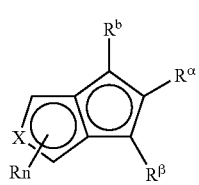
(b)

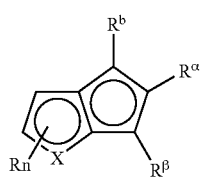
(c)

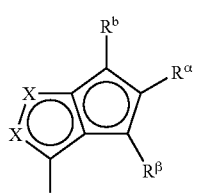
(d)

-continued
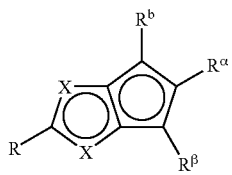 (e)
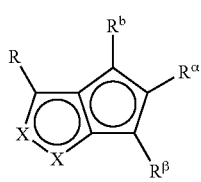 (f)
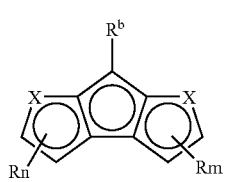 (g)
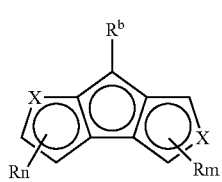 (h)
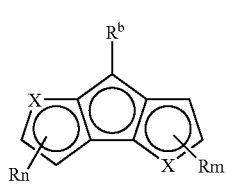 (i)
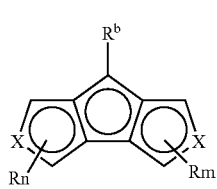 (j)
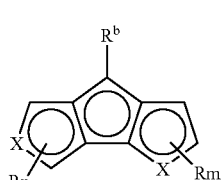 (k)
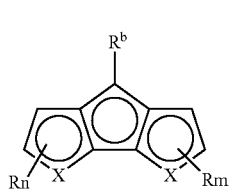 (l)
-continued
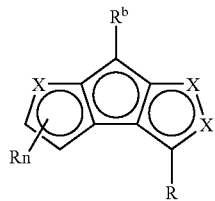 (m)
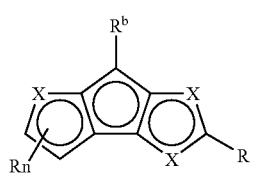 (n)
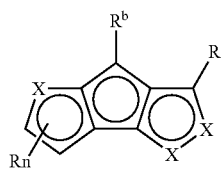 (o)
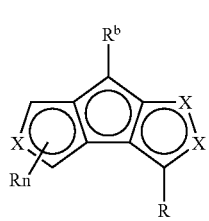 (p)
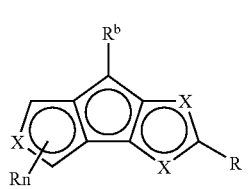 (q)
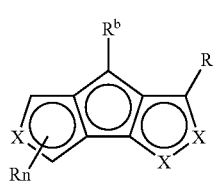 (r)
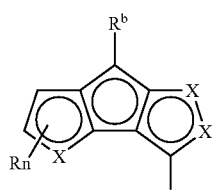 (s)
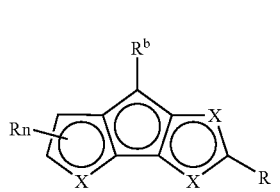 (t)

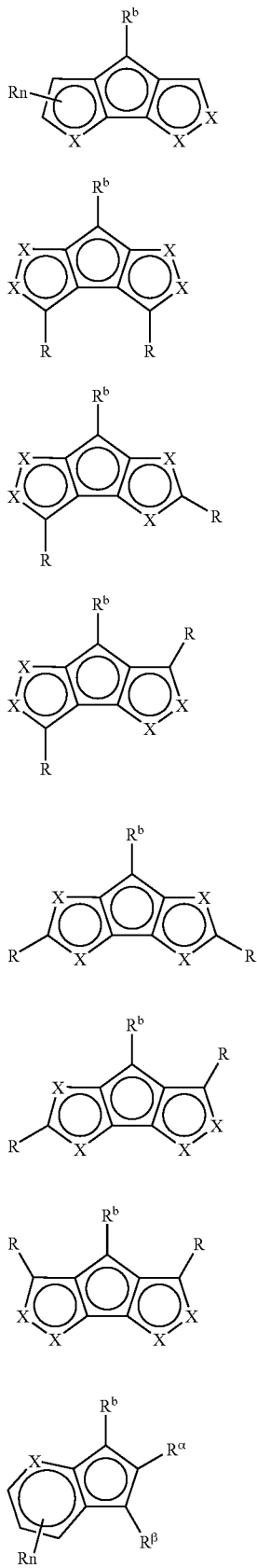
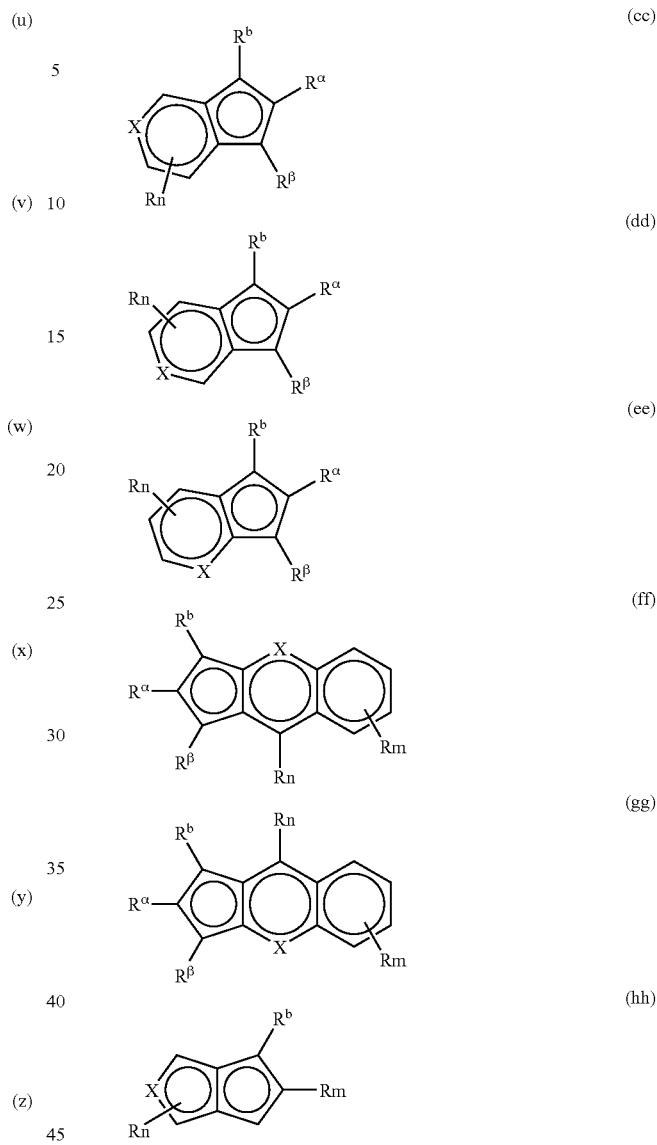

wherein:
(i) the X atoms, the same or different from each other, can be N, P, NR$^g$, PR$^g$, O or S; when a fused ring has two heteroatoms, then one X can be O or S and the other X can be N, P, NR$^g$ or PR$^g$, or one can be N or P and the other can be NR$^g$ or PR$^g$, so that the molecular species represents a chemically viable group;

(i) wherein R$^g$ is a linear or branched $C_1$–$C_{20}$ hydrocarbon radical, optionally substituted with one or more halogen, hydroxy, alkoxy group, a $C_3$–$C_{12}$ cyclohydrocarbon radical, a $C_3$–$C_{12}$ cyclohydrohalocarbon radical, optionally substituted with one or more halogen, $C_6$–$C_{20}$ aryl radical, $C_7$–$C_{20}$ alkylaryl radical, $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical or a halogen atom;

(ii) the R groups, same or different from each other, can be hydrogen, a linear or branched $C_1$–$C_{20}$ hydrocarbon radical, optionally substituted with one or more halogen, hydroxy, alkoxy, a $C_3$–$C_{12}$ cyclohydrohalocarbon radical, optionally substituted with one or more halogen, an $C_6$–$C_{20}$ aryl radical, an $C_7$–$C_{20}$ alkylaryl radical, an $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical or a halogen atom, two adjacent R groups can form together a saturated, unsaturated, or aromatic fused ring;

(iii) n and m are integers which have values from 0 to the maximum number of substituents that the ring can accommodate (e.g. for formulae (a)–(b), n can be 0, 1 or 2); and (iv) $R^\alpha$ and $R^\beta$ representing $\alpha$ and $\beta$ substituents respectively, same or different from each other, can be hydrogen, a linear or branched $C_1$–$C_{20}$ hydrocarbon radical, optionally substituted with one or more halogen, hydroxy or alkoxy, a $C_3$–$C_{12}$ cyclohydrocarbon radical, optionally substituted with one or more halogens, an $C_6$–$C_{20}$ aryl radical, an $C_7$–$C_{20}$ alkylaryl radical, an $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical or a halogen atom; two adjacent $R^\alpha$ and $R^\beta$ groups can form together a saturated, unsaturated, or aromatic fused ring;

(v) $R^a$ and $R^b$ have the meanings reported above.

In its broadest form, the process of the present invention involves polymerizing an addition polymerizable monomer, such as an α-olefin, either alone or together with other addition polymerizable monomers, in the presence of the catalytic system of the invention, including at least one metallocene of formula (I) and a co-catalyst, such as an alumoxane.

The present invention further provides a process for producing tactioselective and even tactiospecific polymers comprising contacting at least one polymerizable monomer with a catalytic system of the invention including at least one metallocene of formulae (III) and/or (IV), where the ligands of said metallocenes bear tacticity controlling α and β substituents, as described herein.

Many metallocenes of formulae (I), (III) and (IV) that are capable of producing tactioselective and/or tactiospecific polymers when contacted with monomers capable of forming polymers with tacticity, have certain specific substitution requirements, often imparting then actual or pseudo symmetry. The symmetry terms generally used to describe metallocenes that generate tactioselective polymers are described below.

The term bilateral symmetry means that the ligand, such as the HCy group, Op group or Cp group is symmetric with respect to a bisecting mirror plane perpendicular to the plane containing the legend, and bisecting the ligand into two parts with the 2 and 5 and the 3 and 4 positions being in a mirror image relationship respectively (e.g. 3,4-dimethyl-Cp or 2,5-dimethyl-Cp). The term pseudobilateral symmetry means that the 3,4 and 2,5 substituents are of similar but not identical steric bulk. (e.g. methyl and ethyl, phenyl and pyridyl, naphthyl and quinoline, methyl and chloro, hydrogen and fluoro, etc).

The term $C_s$ or pseudo-$C_s$ symmetry means that the entire metallocene is symmetric with respect to a bisecting mirror plane passing through the bridging group and the atoms bonded to the bridging group, i.e. the substituents on each coordinating group of a bridged legend, which are reflectively coupled, are identical or similar. $C_s$ or pseudo-$C_s$ symmetry also means that both coordinating groups are bilaterally or pseudo bilaterally symmetric. Syndioselective metallocenes show $C_s$ or pseudo-$C_s$ symmetry and preferably include two coordinating groups linked together by a divalent bridge (i=1 and j+jj=2 in formula (I)) and the β substituents on one coordinating group are sterically larger than the β substituents on the other coordinating group. For example, (dithia-tricyclo[3.3.1.0.0]unnonatetraenyl)-R"-(Cp) ligands, (dithiatricyclo[3.3.1.0.0]unnonatetraenyl)-R"-(Op) ligands, (dithia-tricyclo[3.3.1.0.0]unnonatetracnyl)R"-(3,4-di-t-butyl Cp) ligand, or (dithia-tricyclo[3.3.1.0.0]unnonatetraenyl)R" (2,5-dimethyl-Cp) ligands have $C_s$ symmetry or pseudo $C_s$ symmetry depending on the location of the two sulfur atoms.

(Dithia-tricyclo[3.3.1.0.0]unnonatetraenyl)-R"-(2-chloro-5-methyl-Cp), ligands (dithia-tricyclo[3.3.1.0.0]unnonatetraenyl)-R"-(3-tbutyl-4-isopropyl-Cp)-ligands or related ligands have pseudo-$C_s$ symmetry. Forming appropriate metallocenes from these ligands will produce catalytic systems capable of yielding polymers with varying degrees of syndiotacticity including polymers with very high degrees of syndiospecificity.

The term $C_2$ or pseudo-$C_2$ symmetry means that the ligand has an axis of $C_2$ symmetry passing through the bridging group and, if the ligand system were confided to a plane, the axis would be perpendicular to the plane containing the ligand. Isoselective metallocenes have generally $C_2$ or pseudo-$C_2$ symmetry and preferably include two coordinating groups linked together by a divalent group (i=1 and j+jj=2 in formula (I)), where at least one β substituent on one coordinating group is bulkier than the β substituent in the same location on the other coordinating group and where only the racemic metallocenes are active isoselective species. For example, rac-bis(N-phenyl-5-methyl-1-azapentalenyl)R" ligands, rac-bis(5-methyl-1-thiapentalenyl)R" ligands and bis(cyclopenta[b]quinoline) R" ligands have $C_2$ symmetry.

Rac-(N-phenyl-5-methyl-1-azapentalenyl)-R"-(3-phenyl-indenyl) ligands and rac(4-phenyl-1-thiapentalenyl)-R"-(3-phenyl-indenyl) have pseudo-$C_2$ symmetry. To produce isoselective metallocenes, the ligands are contacted with an appropriate metallic species which yields a mixture of meso isomers (which yield atactic polymer) and rac isomers (which yield isoselective polymers). The meso and rac isomers can be separated by crystallization or other separation techniques, well known in the art. The synthesis of cyclopenta[b]quinolines is described in Eisch, J. J.; Gadek, F. J, *J. Org. Chem.*, 1971, 36, 2065–2071.

Moreover, isoselective metallocenes can also be prepared that do not have inactive meso forms. Such isoselective metallocenes generally comprise one bilaterally symmetric coordinating group and one asymmetric coordinating group (not bilaterally or pseudo-bilaterally symmetric).

In accordance with this invention, one can also produce olefin copolymers particularly copolymers of ethylene and/or propylene, and other olefins by a suitable choice of metallocenes of formula (I). The choice of metallocenes of the present invention can be used to control comonomer content, as well as other properties of the polymer, such as tacticity for vinyl monomers other than ethylene or ethylene like monomers.

As already reported above, the metallocenes of the present invention comprise one or more rings containing at least one heteroatom, associated with the central six π electron radical which directly coordinates the transition metal. Such associated rings include the following classes of radicals:

(i) the heteroatom(s) is contained in a cyclic substituent linked to one of the atoms of the central radical;

(ii) the heteroatom(s) is contained in a ring fused to the central radical, but is not an endocyclic member of the central radical; or
(iii) the heteroatoms are contained in both a cyclic substituent linked to the central radical and in a ring fused to the central radical. The rings fused to the central radical can be aromatic, non-aromatic, unsaturated and/or unsaturated ring or ring systems. Additionally, the central radical can include the phosphino-boratabenzene radicals (that are prepared according to the procedure described in Quan, R. W. et al, *J. Am. Chem. Soc.,* 1994, 116, 4489).

Examples of heterocyclic ring systems that can be associated with the central radical include, without limitation, any B, N, O, Al, Si, P, S, Ga, Ge, As, Se, In, Sn, Sb or Te, containing group, any group containing two or more of these atoms and preferably any N, O, P, or S containing group or any group containing two or more of these preferred atoms. Not limitative examples include pyrrole, isopyrroles, pyrazole, isoimidazole, 1,2,3-triazole, 1,2,4-triazole, imidazole, indolizine, thiophene, 1,3-dithiole, 1,2,3-oxathiole, 1,2-dithiole, thiazole, isothiazole, 1,2,3-oxadiazole, 1,2,4-oxadiazole, 1,3,4-oxadiazole, 1,2,3,4-oxatriazole, 1,2,3,5-oxatriazole, thionaphthene, isothionaphthene, isoindazole, benzoxazole, anthranil, benzothiophene, naphthothiophene, furane, isobenzofuran, benzofuran, indole, indazole, purine, carbazole, carboline, isothiazole, isoxazole, oxazole, furazan, thienofuran, pyrazinocarbazole, furopyran, pyrazolooxazole, selenazolo-benzothiazole, imidazothiazole, furocinnoline, pyridocarbazole, oxathiolopyrole, imidazotriazine, pyridoimidazo-quinoxaline, sila-2,4-cyclopentadiene, thiapentalenes, azapentalenes and dithiatricyclounnonatetraenes.

Additional HCy radicals include, without limitation, heterocyclic fused ring systems where the heteroatom is not a part of the central Cp rings such as compounds represented by formulae (a) and (s) shown above. Not limitative examples include mono heteroatom containing fluorenes where the heteroatom is in the 1–8 positions (using IUPAC numbering); diheteroatom fluorenes again where the heteroatoms are in the 1–8 positions, mono heteroatom indene where the heteroatom is in the 4–7 positions (IUPAC numbering); diheteroatom indenes again where the heteroatom is in the 4–7 positions. Heterocyclic compounds including thia and aza pentalene type systems or heterocyclic compounds including thia, dithia, aza, diaza and thiaaza systems, having three fused five member rings, where the central five membered ring is an all-carbon cyclopentadienyl ring.

Of course, it should be apparent that certain of these ring systems will not support substituents at the heteroatom. Thus, oxygen and sulfur containing rings will not have substituents attached to the oxygen or sulfur atoms. Additionally, in the case of N, P, and As, where these atoms are part of a double bond, they will not have substituents attached thereto.

The term open-pentadienyl (abbreviated as Op) is intended to refer to all six π electron structures that are centered on five connected atoms in an all cis configuration, but where the five atoms bearing the six π electrons are not part of a five membered ring, i.e., the five atoms do not form a cyclopentadienyl ring system. Of course, all five atoms should be sp² hybridized or in some other hybridization that can support electron delocalization over the five centers. One possible precursor to the Op ligands of this invention is a system where four of the atoms are part of two non-conjugated double bonds connected to and separated by a central atom, where the double bonds contribute two electrons each to the ligand system and the central atom supplies two electrons to the system either directly (as the ion pair of a N or P atom) or through the loss of a removable group, to result in the formation of an anionic center as for a C or Si atom. Of course, other central species could be used as well, including Ge and As.

The open-pentadienyl radical suitable for use in the present invention include Op ligands of formula (V):

wherein:
G is a carbon atom, a nitrogen atom, a silicon atom or a phosphorus atom;
L is a $CR^3R^{3'}$ radical, a $SiR^3R^{3'}$ radical, a $NR^{3''}$ radical, a $PR^{3''}$ radical, an oxygen atom or a sulfur atom and L' is a $CR^4R^{4'}$ radical, a $SiR^4R^{4'}$ radical, a $NR^{4''}$ radical, a $PR^{4''}$ radical, an oxygen atom or a sulfur atom; $R^2$, $R^3$, $R^{3'}$, $R^{3''}$, $R^4$, $R^{4'}$, $R^{4''}$ and $R^5$, the same or different from each other, can be a hydrogen, a linear or branched $C_1$–$C_{20}$ hydrocarbon radical, a linear or branched $C_1$–$C_{20}$ halocarbon radical, a linear or branched $C_1$–$C_{20}$ hydrohalocarbon radical, a linear or branched $C_1$–$C_{20}$ alkoxy radical, a $C_3$–$C_{12}$ cyclohydrocarbon radical, a $C_3$–$C_{12}$ cyclohydrohalocarbon radical, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical or a halogen atom; $R^2$ and $R^3$, $R^{3'}$ or $R^{3''}$ and/or $R^5$ and $R^4$, $R^{4'}$ or $R^{4''}$ can form a 4 to 6 membered ring or a 6 to 20 fused ring systems; $R^3$, $R^{3'}$, or $R^{3''}$ and $R^4$, $R^{4'}$, or $R^{4''}$ can be joined together so that the five numbered atomic centers forming the five centered delocalized six electron ligand are contained in a 7 to 20 membered ring system.

The numbers associated with the five atoms in formula (V) are there to indicate how substituent positions will be addressed in the remainder of the specification. Thus, for those metallocenes having a divalent bridge, said bridge will be bonded to the central atom which is indicated as position 1, in a fashion analogous to the numbering in cyclopentadiene. Additionally, the 2 and 5 positions will sometimes be jointly referred to as the α positions or proximal positions (proximal to the 1 position), while the 3 and 4 positions will sometimes be jointly referred to as the β or distal positions.

The present invention also provides a process for producing polymers and copolymers having varying and controllable properties including high molecular weights at high temperatures, tactioselectivity (including tactiospecificity), stereoregularity, narrow or broad molecular weight distribution, etc. The process comprises polymerizing one or more monomers in the presence of one or more metallocenes of the invention.

The Applicant has found that metallocenes of the present invention can also be prepared which yield stereoregular and stereospecific polymer products, such as linear high molecular weight polyethylene, isotactic polyolefins, syndiotactic polyolefins and hemi-isotactic polyolefins. These uniquely designed metallocenes have as a key feature a bridged specifically substituted legend, containing at least one HCy coordinating group.

For metallocenes that produce stereoselective and/or tactioselective polyolefins, the ligand that forms the metallocene of the present invention can be substituted in such a way that the same metallocene is stereorigid (bridged), stereolocked and stereodirected so that: (1) the substituents on the legend lock and/or direct the polymer chain-end orientation and/or monomer approach such that each successive monomer addition is stereospecific and the degree of stereoselectivity can be controlled; and (2) the bridging group renders the ligand system rigid so that its rotation or isomerization is prevented or restricted. These metallocenes are characterized by having β or distal substituents on the ligands controlling the orientation of monomer addition; moreover, metallocene configuration determines tactioselectivity.

The metallocenes of the present invention can be either non-stereorigid/non-stereolocked, stereorigid/non-stereolocked, non-stereorigid/stereolocked, stereorigid/stereolocked or mixtures thereof. Stereorigidity is imparted to the metallocenes of this invention by a chemical bridge connecting two coordinating groups to form metallocenes of formulae (III) and (IV), i.e. where i=1 and j=1 in the general formula (I). The bridging group prevents or greatly restricts the two coordinating groups from undergoing structural isomerizations or rotation.

The Applicant has also found that, by controlling the metallocenes relative steric size, catalysts can be formed that insert statistically controllable defects into the resulting polymers. The Applicant has also found that catalysts of the present invention can be designed to produce hemi-isotactic polymers. The Applicant has also found that intimate mixtures of polymers with different properties can be prepared by polymerizing monomers in the presence of metallocenes of the present invention or polymerizing monomers in the presence of catalysts of this invention in combination with prior art catalysts.

In the state of the art, the term metallocene denotes an organometallic coordination compound in which two cyclopentadienyl containing ligands are coordinated to or "sandwiched" about a central metal atom and where all five centers of the Cp ring are involved in metal coordination. The metal atom may be a transition metal or transition metal halide, alkyhalide or alkoxide. Such structures are sometimes referred to as "molecular sandwiches" since the cyclopentadienyl ligands are oriented above and below a plane containing the central coordinated metal atom nearly parallel to the planes containing the Cp ring. Similarly, the term "cationic metallocene" means a metallocene in which the central coordinated metallic species carries appositive charge, i.e., the metallocene complex is a cation associated with a stable non-coordinating or pseudo non-coordinating anion.

However, in addition to the traditional meaning of the term metallocene, the present invention expands this term to encompass metallocenes where at least one of the groups coordinating the central metal atom or ion is a ring system containing at least on heteroatom, associated with the central radical (the central radical directly coordinates the transition metal). The second coordinating group can be a ring system having the meanings of the first coordinating group or a heterocyclic containing group where the heteroatom is in the central ring, an Op containing ligand or a Cp containing ligand, a nitrogen ligand, a phosphorus ligand, an oxygen ligand or a sulfur ligand.

One skilled in the art should also recognize that the permissible values for i, j, k and l will depend on the actual ligand and on the coordinating metal; these values are understood to conform to known organometallic structural and electronic requirements.

Suitable Z radicals for use in the present invention include, without limitation, radicals represented as follows:
(1) heterocyclic containing ligands where the heteroatom is contained in the central radical;
(2) Op containing ligands;
(3) cyclopentadienyl or substituted cyclopentadienyl radicals of formula $(C_5R'_{iii})$, wherein the groups R', same or different from each other have the meanings of R, and two adjacent R' groups can be joined together to form a $C_4$–$C_6$ ring; iii is an integer having a value from 0 to 5;
(4) nitrogen and phosphorus containing radicals, represented by the formula $(JR^6_{jjj})$ where J is nitrogen or phosphorus atom, the $R^6$ groups, same or different from each other, have the meanings described above for radicals $R^1$–$R^5$; jjj is an integer having a value from 1 to 3; or
(5) an oxygen or sulfur containing radical represented by the formula $(UR^7_{kkk})$, where U is oxygen or sulfur atom and where $R^7$ is a radical as described above for radicals $R^1$–$R^5$; and kkk is an integer having a value of 0 or 2.

Suitable structural bridging groups R" able to impart stereorigidity to the metallocenes of this invention, include, without limitation, a linear or branched $C_1$–$C_{20}$ alkenyl radical, a $C_3$–$C_{20}$ dialkyl methyl radical, a $C_3$–$C_{12}$ cyclohydrocarbon radical, an $C_6$–$C_{20}$ aryl radical, a diarylmethylene radical, a diaryl allyl radical, a silicon hydrocarbon radical, dihydrocarbon silenyl radical, a germanium hydrocarbyl radical, a phosphorous hydrocarbon radical, a nitrogen hydrocarbon radical, a boron hydrocarbon radical and an aluminum hydrocarbon radical.

Other suitable bridging groups R" include ionic units, such as $B(C_6F_5)_2$ and $Al(C_6F_5)_2$, and $R_2C$, $R_2Si$, $R_4Et$, $R_6Pr$, where R can be any hydrocarbon, cyclic hydrocarbon, cyclic or linear hydrocarbon bearing another organometallic catalyst or carboranes. Indeed, the bridges can be $C_2$ bridges (and $C_3$ etc.) which form the backbone of polymeric supports (e.g. the atactic, syndiotactic and isotactic polymers from vinyl-indene and 9-vinyl-fluorene etc.) as well as functionalized polystyrene precursors and all other polymers with terminal or branched boron or Al functional groups which are bonded to the catalysts, e.g., in zwitterionic form. $R_2C$ and $R_2Si$ bridging groups are preferred with isopropylidene and dimethylsilenyl bridging groups being particularly preferred.

Suitable radicals corresponding to R, R', $R^1$–$R^5$, $R^\alpha$ and $R^\beta$ include, without limitation, hydrogen atoms, linear or branched $C_1$–$C_{20}$ hydrocarbon radicals, linear or branched $C_1$–$C_{20}$ halocarbyl radicals, linear or branched $C_1$–$C_{20}$ hydrohalocarbon radicals, linear or branched $C_1$–$C_{20}$ alkoxy radicals, $C_3$–$C_{12}$ cyclohydrocarbon radicals, a $C_3$–$C_{12}$ cyclohydrohalocarbon radicals, aryl radicals, allylaryl radicals, arylalkyl radicals, silicon hydrocarbon radicals, germanium hydrocarbon radicals, phosphorus hydrocarbon radicals, nitrogen hydrocarbon radicals, boron hydrocarbon radicals, aluminum hydrocarbon radicals and halogen atoms. Preferable, said radicals are linear or branched $C_1$–$C_{20}$ alkyl radicals, trialkylsilyl radicals and aryl radicals, where linear or branched $C_1$–$C_{10}$ radicals and aryl radicals are particularly preferred; methyl, ethyl, isopropyl, trialkylmethyl radicals, trialkylsilyl radicals, and phenyl radicals are especially preferred.

Additionally, suitable radicals corresponding to R, R', $R^1$–$R^5$, $R^\alpha$ and $R^\beta$ include, without limitation, zwitterionic radicals such as Cp-B($C_6F_5$)$_3^-$, Cp-Al($C_6F_5$)$_3^-$, Cp-Al($CF_3$)$_3^-$, Cp-X—Al($C_6F_5$)$_3^-$ and Cp-X—B($C_6F_5$)$_3^-$, where X can represent an alkenyl group or an alkenoxy group.

The metallocenes of this invention containing zwitterionic radicals on either one of the coordinating group the ligand of the present invention and having Me=metal of group 4 do not need an independent and sometimes stereochemically interfering counterion (i.e., l=0). These zwitterionic radicals may also be suitable for mono and di cations of metallocenes of formula (I) where Me is a group 5 metal in the plus five oxidation state (Me(V)). They could even conceivably be used to create ion-pair metallocenes with the normally neutral group 3 metals in the plus three oxidation state (Me(III)). In this case, one could obtain heterogeneous insoluble ion-pair systems for improved polymer particle size and morphology control.

Preferred metals corresponding to Me include, without limitation, Group 3, 4, or 5 elements or lanthanide elements from the Periodic Table of Elements. More preferably, Me is a Group 4 or 5 metal, titanium, zirconium and hafnium being the most preferred. Preferred lanthanide elements are Lu, La, Nd, Sm and Gd.

Suitable hydrocarbon radicals or halogens corresponding to Q include, without limitation, a linear or branched $C_1$–$C_{20}$ alkyl radical, an aryl radical, an alkylaryl radical, an arylalkyl radical, F, Cl, Br and I. Q is preferably methyl or halogen, and more preferably chlorine atom.

Exemplary hydrocarbon radicals are methyl, ethyl, propyl, butyl, amyl, isoamyl, hexyl, isobutyl, heptyl, octyl, nonyl, decyl, cetyl, 2-ethylhexyl and phenyl. Exemplary alkylene radicals are methylene, ethylene, propylene and isopropylidenyl. Exemplary halogen atoms include fluorine, chlorine, bromine and iodine, chlorine being preferred. Examples of the alkylidene radicals are methylidene, ethylidene and propylidene. Exemplary nitrogen containing radicals include amines such as alkyl amines, aryl amines, arylalkyl amines and alkylaryl amines.

Suitable non-coordinating anions corresponding to P in the general formula include, without limitation, [$BF_4$]$^-$, B($PhF_5$)$^-_4$, [W($PhF_5$)$_6$]$^-$, [Mo($PhF_5$)$_6$]$^-$ (wherein $PhF_5$ is pentafluorophenyl), [$ClO_4$]$^-$, [$S_nO_6$]$^-$, [$PF_6$]$^-$, [$SbR_6$]$^-$ and [$AlR_4$]$^-$; wherein each R is independently Cl, a $C_1$–$C_5$ alkyl group (preferably a methyl group), an aryl group (e.g. a phenyl or substituted phenyl group) or a fluorinated aryl and alkyl group.

Tactioselective metallocenes (i.e. metallocenes that produce tactioselective polymers) of the present invention are generally characterized by having symmetry or pseudo symmetry associated with the ligand or the metallocene. As stated previously, metallocenes including two ligands and having $C_2$ or pseudo-$C_2$ symmetry or having one bilaterally symmetric ligand and one asymmetric ligand and at least one bulky β-substituent or pseudo β-substituent (in the case of metallocenes having non-Cp groups such as constrained geometry amine or phosphine anionic ligands) produce polymers with varying degrees of isotacticity. In contrary, metallocenes including two ligands and having $C_s$ or pseudo-$C_s$ symmetry produce polymers with varying degrees of syndiotacticity. Preferably, the ligands are bridged, but certain non-bridged two metallocenes can give polymers with varying tactioselectivity or polymers with varying degrees of regularity in the mode of monomer addition, e.g., head-to-tail or tail-to-head addition regularity.

Of the metallocenes of this invention, titanocenes, zirconocenes and hafniocenes are most preferred. The present invention also encompasses La, Lu, Sm, Nd and Gd metallocenes.

A few exemplary metallocenes of the present invention are metallocenes where:
(1) Y, in the YR"Z ligand, corresponds to formulae (a)–(s) where $R^β$ is a bulky substituent or where the R substituent in combination with the ring atom β to the carbon attached to R" forms a bulky β substituent; or
(2) the two Y groups in the YR"Y ligand, same or different from each other, corresponds to formulae (a)–(s), where $R^β$ is a bulky substituent or where the R substituent in combination with the ring atom β to the carbon attached to R" forms a bulky β substituent.

A few exemplary metallocenes of the present invention are metallocenes where:
(1) Y, in the YR"Z ligand, corresponds to formulae (a)–(s) and Z is a Cp radical; Y and Z are bilaterally symmetric and only one of either Y or Z has two bulky β substituents; or
(2) the two Y groups, in the YR"Y ligand, same or different from each other are bilaterally symmetric and correspond to formulae (a)–(s), where only one of the Y group has two bulky β substituents.

Yet another important subclass metallocenes of this invention are those capable of producing partially crystalline thermoplastic-elastomeric propylene polymers, directly obtainable from the polymerization reaction of propylene without the need of separation steps or of sequential polymerization, which are endowed with good mechanical properties and can be suitably used as elastomeric materials and as compatibilizers for blends of amorphous and crystalline polyolefins.

Said metallocenes are unbridged metallocenes corresponding to formula (I) wherein i=0, j=1, jj=1 (i.e. containing two unbridged ligands) having specific substitution patterns, thus obtaining polypropylenes having isotactic and atactic blocks within a single polymer chain, or blends of isotactic and atactic polymer chains, exhibiting elastomeric properties.

In formula (I), Y and Z, equal or different from each other, are preferably unbridged ligands corresponding to formula (hh)':

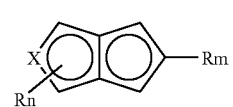

(hh)' wherein X, R, n and m have the meanings reported above.

Said metallocenes are not rigid and upon isomerisation the catalyst symmetry alternates between a chiral and an achiral geometry; the geometry alternation in the metallocenes of the invention can be controlled by selecting suitable bulky unbridged ligands Y and Z, as well as suitable polymerization conditions:

Non limiting examples of the above described metallocenes are:

bis(4-phenyl-2,6-dimethyl-thiopentalene)zirconium dichloride;

bis(4-phenyl-2,6-diethyl-thiopentalene)zirconium dichloride;

bis(4-phenyl-2,6-dipropyl-thiopentalene)zirconium dichloride;

bis(4-phenyl-2,6-di-i-propyl-thiopentalene)zirconium dichloride;

bis(4-phenyl-2,6-di-n-butyl-thiopentalene)zirconium dichloride;
bis(4-phenyl-2,6-di-t-butyl-thiopentalene)zirconium dichloride;
bis(4-phenyl-2,6-di-trimethylsilyl-thiopentalene)zirconium dichloride;
bis(4-(2-pyridyl)-2,6-dimethyl-thiopentalene)zirconium dichloride;
bis(4-(3-pyridyl)-2,6-dimethyl-thiopentalene)zirconium dichloride;
bis(4-(8-chinolyl)-2,6-dimethyl-thiopentalene)zirconium dichloride;
bis(4-(3-chinolyl)-2,6-dimethyl-thiopentalene)zirconium dichloride;
bis(4-(5-pyrimidyl)-2,6-dimethyl-thiopentalene)zirconium dichloride;
bis(4-(2-furanyl)-2,6-dimethyl-thiopentalene)zirconium dichloride;
bis(4-(2-pyrolyl)-2,6-dimethyl-thiopentalene)zirconium dichloride;
bis(4-(3,5-dimethylphenyl)-2,6-dimethyl-thiopentalene)zirconium dichloride;
bis(4-(3,5-diethylphenyl)-2,6-dimethyl-thiopentalene)zirconium dichloride;
bis(4-(3,5-dimethylsilylphenyl)-2,6-dimethyl-thiopentalene)zirconium dichloride;
bis(4-methyl-2,6-dimethyl-thiopentalene)zirconium dichloride;
bis(4-phenyl-2,6-dimethyl-thiopentalene)zirconium dichloride;
bis(4-(trifluoromethyphenyl)-2,6-dimethyl-thiopentalene)zirconium dichloride;
bis(4-naphthyl-2,6-dimethyl-thiopentalene)zirconium dichloride;
bis(4-(1-indenyl)-2,6-dimethyl-thiopentalene)zirconium dichloride;
bis(4-phenyl-2,6-dimethyl-azapentalene)zirconium dichloride;
bis(4-phenyl-2,6-diethyl-azapentalene)zirconium dichloride;
bis(4-phenyl-2,6-dipropyl-azapentalene)zirconium dichloride;
bis(4-phenyl-2,6-di-i-propyl-azapentalene)zirconium dichloride;
bis(4-phenyl-2,6-di-n-butyl-azapentalene)zirconium dichloride;
bis(4-phenyl-2,6-di-t-butyl-azapentalene)zirconium dichloride;
bis(4-phenyl-2,6-di-trimethylsilyl-azapentalene)zirconium dichloride;
bis(4-(2-pyridyl)-2,6-dimethyl-azapentalene)zirconium dichloride;
bis(4-(3-pyridyl)-2,6-dimethyl-azapentalene)zirconium dichloride;
bis(4-(8-chinolyl)-2,6-dimethyl-azapentalene)zirconium dichloride;
bis(4-(3-chinolyl)-2,6-dimethyl-azapentalene)zirconium dichloride;
bis(4-(5-pyrimidyl)-2,6-dimethyl-azapentalene)zirconium dichloride;
bis(4-(2-furanyl)-2,6-dimethyl-azapentalene)zirconium dichloride;
bis(4-(2-pyrolyl)-2,6-dimethyl-azapentalene)zirconium dichloride;
bis(4-(3,5-dimethylphenyl)-2,6-dimethyl-azapentalene)zirconium dichloride;
bis(4-(3,5-diethylphenyl)-2,6-dimethyl-azapentalene)zirconium dichloride;
bis(4-(3,5-dimethylsilylphenyl)-2,6-dimethyl-azapentalene)zirconium dichloride;
bis(4-methyl-2,6-dimethyl-azapentalene)zirconium dichloride;
bis(4-phenyl-2,6-dimethyl-azapentalene)zirconium dichloride;
bis(4-(trifluoromethyphenyl)-2,6-dimethyl-azapentalene)zirconium dichloride;
bis(4-naphthyl-2,6-dimethyl-azapentalene)zirconium dichloride;
bis(4-(1-indenyl)-2,6-dimethyl-azapentalene)zirconium dichloride;
bis(4-phenyl-2,6-dimethyl-phosphapentalene)zirconium dichloride;
bis(4-phenyl-2,6-diethyl-phosphapentalene)zirconium dichloride;
bis(4-phenyl-2,6-dipropyl-phosphapentalene)zirconium dichloride;
bis(4-phenyl-2,6-di-i-propyl-phosphapentalene)zirconium dichloride;
bis(4-phenyl-2,6-di-n-butyl-phosphapentalene)zirconium dichloride;
bis(4-phenyl-2,6-di-t-butyl-phosphapentalene)zirconium dichloride;
bis(4-phenyl-2,6-di-trimethylsilylphosphapentalene)zirconium dichloride;
bis(4-(2-pyridyl)-2,6-dimethyl-phosphapentalene)zirconium dichloride;
bis(4-(3-pyridyl)-2,6-dimethyl-phosphapentalene)zirconium dichloride;
bis(4-(8-chinolyl)-2,6-dimethyl-phosphapentalene)zirconium dichloride;
bis(4-(3-chinolyl)-2,6-dimethyl-phosphapentalene)zirconium dichloride;
bis(4-(5-pyrimidyl)-2,6-dimethyl-phosphapentalene)zirconium dichloride;
bis(4-(2-furanyl)-2,6-dimethyl-phosphapentalene)zirconium dichloride;
bis(4-(2-pyrolyl)-2,6-dimethyl-phosphapentalene)zirconium dichloride;
bis(4-(3,5-dimethylphenyl)-2,6-dimethyl-phosphapentalene)zirconium dichloride;
bis(4-(3,5-diethylphenyl)-2,6-dimethyl-phosphapentalene)zirconium dichloride;
bis(4-(3,5-dimethylsilylphenyl)-2,6-dimethyl-phosphapentalene)zirconium dichloride;
bis(4-methyl-2,6-dimethyl-phosphapentalene)zirconium dichloride;
bis(4-phenyl-2,6-dimethyl-phosphapentalene)zirconium dichloride;
bis(4-(trifluoromethyphenyl)-2,6-dimethyl-phosphapentalene)zirconium dichloride;
bis(4-naphthyl-2,6-dimethyl-phosphapentalene)zirconium dichloride; and
bis(4-(1-indenyl)-2,6-dimethyl-phosphapentalene)zirconium dichloride.

Indeed, the metallocenes can be tailored using a number of strategies to control properties, such as the relative stereoselectivity and/or stereospecificities, the molecular weight, and other significant polymer properties. Metallocenes having a single carbon bridged ligands have been more stereospecific than the silicon bridged analogs for syndiotactic specific catalysts; the carbon bridged metallocenes are generally less stereospecific than the silicon bridged analogs for isospecific catalysts. The larger the steric requirements are for the β-substituents, the more stereospecific the metallocene is. The difference in the steric requirements for the conformational locks and the stereo-controlling β-substituent can be used to optimize the orientation of the chain end. And substituents at the α-position should result in increased polymer molecular weight.

The present invention is directed to both neutral metallocenes and cationic metallocenes as evidenced by the subscript l associated with the anion P having permissible values of 0 to 2, i.e., when l=0, the metallocenes are neutral and when l=1 or 2 the metallocenes are cationic, as evidenced by the inclusion of an anion is the general formula.

The metallocenes of the present invention can also be designed to produce polymers with very high tacticity indices depending on the desired tacticity. In order to produce tactically specific polymers from metallocenes of the present invention, the characteristics of the β-substituents on the bridged ligands are important. Thus, the "steric requirement" or "steric size" of the β-substituents can be designed to control the steric characteristics of metallocenes, so that the arrangement of β-substituents allows control of the stereochemistry of each successive monomer addition.

It may also be possible to strategically arrange substituents with the proper steric properties on an appropriate carbon(s) of the metallocene of the present invention which should serve as chain end conformational locks (preferably positioned in the mouth of the ligand) and which could also confer solubility (ion pair separation for better catalyst activity and stereospecificity) and/or insolubility (for better control of polymer morphology), as desired. The bridged, substituted metallocenes are stereorigid, provide chain-end conformational locks, and are superior to those without such conformational locks.

Prior art has shown, for example, that a methyl substituent positioned at the α-Cp position on the $C_5$ ring of bisindenyl catalysts increases the molecular weight of isotactic polypropylene produced with the Et[Ind]$_2$ZrCl$_2$ based catalyst. Similarly, a methyl substituent on the C6 ring of the indenyl ring system has reduced the stereospecificity; depending on the positional isomerism.

Moreover, the addition of methyl, t-Bu, OMe and Ph substituents to the coordinating groups of the ligand and to the bridging group R" have had steric, solubility and electronic influences on catalysts in syndiotactic and isotactic specific polymerizations.

By making the sterically larger β-substituents different and/or the sterically smaller β-substituents different, the tactioselective versions of the metallocenes of the present invention can be designed to impart any degree of tacticity to the resulting polymers. Thus, if one β-substituent is t-butyl and another is ethyl, and the other two are methyls, the tactiospecificity of the metallocenes will be reduced relative to the one having two t-butyls and two methyls.

Of course, cationic metallocenes require the anion P to maintain their net neutrality. The anion P in the general formula is preferentially a compatible non-coordinating or pseudo-non-coordinating anion that either does not coordinate with the metallocene cation or only weakly coordinates to the cation, yet remains sufficiently labile so that it can be readily displaced by a neutral Lewis base such as a monomer unit. Compatible non-coordinating or pseudo-noncoordinating anions are described as anions that stabilize the cationic metallocenes, but do not transfer an electron or electron equivalent to the cation to produce a neutral metallocene and a neutral byproduct of the non-coordinating or pseudo-non-coordinating anion.

The useful size of the counterion P also depends on the bulkiness or steric requirements of the ligands. In addition to size, other characteristics are important for good anions or counterions, such as stability and bonding. The anion must be sufficiently stable so that it cannot be rendered neutral by virtue of the metallocene cation electron extraction and the bond strength with the cation must be sufficiently week not interfere with monomer coordination and chain propagation.

A preferred procedure for producing cationic metallocenes of the present invention (l=1 or 2) involves the reaction of an ion-pair in a non-coordinating solvent with a metallocene of formula (I), where l=0. For example, triphenylcarbenium tetrakis(pentafluorophenyl)boronate or a similar ion-pair may be reacted with a neutral metallocene of the present invention in a solvent such as toluene to generate the corresponding cationic metallocene. This preparation method is well known in the state of the art, as described for instance in U.S. Pat. No. 5,225,550.

A preferred application of the present invention is in the polymerization of alpha olefins, preferably ethylene and propylene, to produce highly linear, low, medium and high density polyethylene, as well as atactic, isotactic, syndiotactic, hemi-isotactic polypropylenes or mixtures thereof. However, the metallocenes of the invention may be used in the preparation of hemi-isotactic, isotactic or syndiotactic polymers obtained from other ethylenically unsaturated monomers. For example, syndiospecific, isospecific or hemi-isospecific polymers of 1-butene, 1-pentene, 1-hexene and styrene can be prepared using the metallocenes of the present invention.

Addition polymerizable monomers suitable for use in this invention include ethylenically unsaturated monomers or any organic molecule having a terminal vinyl group ($CH_2$=CH), such as α-olefins (e.g. propylene, 1-butene, 1-pentene, 1-hexene, 4-methyl-1-pentene), vinyl halides (e.g. vinyl fluoride and vinyl chloride), vinyl arenes (e.g. styrene, alkylated styrenes, halogenated styrenes and haloalkylated styrenes), dienes (e.g. 1,3-butadiene and isoprene). Polyethylene and polypropylene are probably of the greatest practical significance and the invention will be described in detail with reference to the production of polyethylenes and/or polypropylene polymers, but it should be understood that this invention is generally applicable to all addition polymerizable monomers. These catalysts may also be useful in the polymerization of dienes to elastomers through the inclusion of 1,4-addition instead of 1,2-addition. Of course, these catalysts may also be useful in varying the relative amounts of 1,2-addition versus 1,4-addition polymers containing conjugated diene monomers.

The polymerization procedure using the metallocenes according to the present invention is carried out according to procedures known in the art, such as the one disclosed in U.S. Pat. No. 4,892,851.

In the catalytic systems according to the present invention the metallocenes according to the present invention are used in association with various co-catalysts. Although many of the species are active alone, they can be activated upon the addition of various cocatalysts. Co-catalysts, usually organo-aluminum compounds such as trialkylaluminum, trialkyloxyaluminum, dialkylaluminum halides or alkylaluminum dihalides may be used in the present invention. Especially suitable alkylaluminums are trimethylaluminum and triethylaluminum (TEAL), the latter being the most preferred. Methylalumoxane (MAO) is also usable in carrying out the methods of the present invention, especially for neutral metallocenes, in amounts well in excess of the stoichiometric equivalent.

The alumoxanes are polymeric aluminum compounds which can be represented by the general formulae (R—Al—O)$_n$, which is a cyclic compound, and R(R—Al—O—)$_n$—AlR$_2$, which is a linear compound, where R is a C$_1$-C$_5$ alkyl group, such as methyl, ethyl, propyl, butyl and pentyl, and n is an integer from 1 to 20. Most preferably, R is methyl and n is 4.

Generally, in the preparation of alumoxanes from aluminum trialkyl and water, a mixture of the linear and cyclic compounds is obtained. The alumoxane can be prepared in various ways. Preferably, they are prepared by contacting water with a solution of aluminum trialkyl, such as, for example, aluminum trimethyl, in a suitable organic solvent, such as benzene or an aliphatic hydrocarbon. For example, the aluminum alkyl is treated with water in the form of a moist solvent. In an alternative method, the aluminum alkyl can be contacted with a hydrated salt, such as hydrated copper sulfate. Preferably, the alumoxane is prepared in the presence of a hydrated copper sulfate: a dilute solution of aluminum trimethyl in toluene is treated with copper sulfate represented by the general formula CuSO$_4$.5H$_2$O. The ratio of copper sulfate to aluminum trimethyl is desirably about 1 mole of copper sulfate for 4 to 5 moles of aluminum trimethyl. The reaction is evidenced by the evolution of methane.

The ratio of aluminum in the alumoxane to total metal in the metallocene can be in the range of 0.5:1 to 10,000:1, and preferably 5:1 to 1000:1. The solvents used in the preparation of the catalytic systems of the invention are preferably inert hydrocarbons, in particular hydrocarbons inert with respect to the metallocene.

Such solvents are well known and include, for example, isobutane, butane, pentane, hexane, heptane, octane, cyclohexane, methylcyclohexane, toluene and xylene. As a further control and refinement of polymer molecular weight, one can vary the alumoxane concentration: higher concentrations of alumoxane in the catalytic system of the invention result in higher polymer product molecular weight.

Since, in accordance with this invention, one can produce high viscosity polymer products at relatively high temperature, temperature does not constitute a limiting parameter as with the prior art metallocene/alumoxane catalyst. The catalytic systems described herein, therefore, are suitable for the polymerization of olefins in solution, slurry or gas phase polymerizations and over a wide range of temperatures and pressures. For example, such temperatures may be in the range of –60° C. to 280° C. and preferably in the range of 50° C. to 160° C. The pressures employed in the process of the present invention are those usually employed in the state of the art, preferably in the range of 1 to 500 atmospheres and greater.

In a solution phase polymerization, the alumoxane is preferably dissolved in a suitable solvent, typically an inert hydrocarbon solvent such as toluene and xylene, in molar ratios of about 5×10$^{-3}$ M. However, greater or lesser amounts can be used. The soluble metallocenes of the invention can be converted to supported heterogeneous catalytic systems by depositing said metallocenes on catalyst supports known in the art, such as silica, alumina and polyethylene. The solid catalytic systems, in combination with an alumoxane, can be usefully employed in slurry and gas phase olefin polymerizations.

After polymerization and deactivation of the catalyst, the obtained polymer can be recovered by processes well known in the art for removal of deactivated catalysts and solution. The solvents may be flashed off from the polymer solution and the polymer obtained extruded into water and cut into pellets or other suitable comminuted shapes. Pigments, antioxidants and other additives, as is known in the art, may be added to the polymer.

The polymer product obtained in accordance with the process of the invention have a weight average molecular weight ranging from about 500 to about 1,400,000 and preferably from about 1000 to 500,000. The molecular weight distribution (Mw/Mn) ranges preferably from 1.5 to 4, but higher values can be obtained. The polymers contain 1.0 chain end unsaturation per molecule. Broadened MW can be obtained by employing two or more of the metallocenes of this invention in combination with the alumoxane. The polymers produced by the process of this present invention are capable of being fabricated into a wide variety of articles, as is known for polymer products derived from addition polymerizable monomers.

The metallocene used in the present invention may be prepared by procedures known in the art, as disclosed in U.S. Pat. No. 4,892,851, while the active cationic metallocenes may be produced by simply converting the neutral metallocenes into the cationic state following known procedures, such as those disclosed in EP 0 277 003 and 0 277 004 or by reaction with triphenylcarbenium boronates. Similarly, alcohol—B(PhF$_5$)$_3$ complexes can be used as anionic precursors for preparing the active cationic metallocenes of the present invention where the alcoholic proton reacts with an amine of an alkyl group on the coordinating metal atoms to generate a cationic metallocene and an alkoxide—B(PhF$_5$)$_3$ anion.

The metallocenes of this invention can also be converted to supported heterogeneous catalytic systems by depositing the catalysts on supports including, without limitation, silica, alumina, magnesium dichloride and polystyrene beads. Supported metallocenes can improve the bulk density of the polymer, as further described in U.S. Pat. Nos. 4,935,474 and 4,530,914, and EP 0 427 697 and 0 426 638.

The metallocenes of the invention can also be chemically linked to support by placing functional groups with ion pairs or Lewis acid centers or Lewis base centers on the ligands and/or supports. Supporting can also be achieved by using large (oligomeric or polymeric) insoluble anions as counter ions.

The metallocene of the present invention can be used to prepare low, medium and high molecular weight polymers, low, moderate and high density polymers, elastomers, aspecific, isospecific, syndiospecific and/or hemi-isospecific polymers, not only of propylene, but of all α-olefins, such as 1-butene, 1-pentene, 1-hexene, 4-methyl-1-pentene and CH$_2$=CH(CH$_2$)$_p$Si(CH$_3$)$_3$ where p is 1 to 4. Additionally, the metallocenes of this invention can polymerize singly or in mixtures all addition polymerizable monomers including vinyl monomers and diene monomers.

One of ordinary skill should recognize that the metallocenes of the invention, that can give rise to isoselective catalysts, can be separated into a meso form, which is asymmetric, and a rac form that is selective to isotactic polymers. The stereospecific rac metallocenes can be separated from the meso form by crystallization. It is well known from the Bercaw et al. (*J. Ann. Cherry Soc.* 1992, 1 14, 7607 J. E. Bercaw and E. B. Coughlin.) that rac-metallocenes, free of the undesirable aspecific meso stereoisomers, can be prepared by placing suitable bulky substituents, such as Si(Me)$_3$, on the ligand atoms in α position to the bridgehead atom.

The metallocenes of the present invention can be used alone or in mixture with other metallocene catalysts, TiCl$_3$/DEAC and/or TiCl$_4$/MgCl$_2$/TEAL catalysts having internal electron donors such as diisobutylypthalate, and external donors, such as diphenyldimethoxysilane and methanol to produce polymers with mixed stereochemical compositions, distributions or tailored molecular weight distributions. Reactor blends of polymers with optimized physical, thermal, mechanical and rheological properties can be tailored to produce the optimum mixture for specific applications requiring high melt strength, high clarity, high impact strength and high rates of crystallization, simply by mixing catalytic species together in appropriate ratios.

The metallocenes of the present invention influence the rate of termination by β-hydride elimination reactions. This, therefore, provides a novel ligand effect for controlling polymer molecular weights. These metallocenes can be exploited to tailor molecular weights and hence molecular weight distributions with mixed species of the catalysts and any other class of catalysts. This would be advantageous in tailoring the polymer properties in HDPE, LLDPE, i-PP, s-PP, etc. Similarly the chain-end conformation locking substituent will influence the rate of reactivity of the new metallocenes with α-olefins such as propylene, butene and hexene. The new ligand effects on the catalyst reactivity ratios can be exploited to produce reactor blends with varying compositions, sequences, distributions and/or molecular weight distributions. The metallocenes of the present invention provide improved tailored grades of polypropylene and propylene-ethylene high impact copolymers, as reactor blends or from reactors in series, including fluidized and stirred gas phase polymerizations.

The metallocenes of the present invention can also be used to produce copolymers of olefins and copolymers of olefins and dienes with varying degrees of tactiospecificity.

Hereinafter is described a general process for the preparation of the metallocenes of the present invention. In said process, it is important that the metallocene is "pure", because low molecular weight, amorphous polymers can be produced by impure metallocenes.

Generally, the preparation of metallocenes comprises forming and isolating the ligand (bridged or unbridged), which is then aromatized or deprotonated to form a delocalized electron system or an hetero anion, and subsequently reacted with a metal halide or alkylide to form the final complex.

The synthesis procedures are generally performed under an inert gas atmosphere, using a glove box or Schlenk techniques. The synthesis process generally comprises the steps of 1) preparing the halogenated or alkylated metal compound, 2) preparing the ligand, 3) synthesizing the complex, and 4) purifying the complex.

The synthesis of the bridged ligands of the present invention having the β-substituted Cp can be prepared by contacting a suitable substituted fulvene with a suitable substituted cyclopentadienyl containing an anion ring, under reaction conditions sufficient to produce a bridged structure, to yield ligands with either $C_2$ or $C_s$ or pseudo-$C_2$ or pseudo $C_s$ symmetry.

Fulvene is cyclopentadiene with an exo-cyclic methylene group at the 1 position of cyclopentadiene ring. The exocyclic methylene carbon is the 6 position of fulvene. Since this carbon can ultimately become the bridging group R" in formula (I), the preferred fulvenes for the preparation of the present metallocenes are 6,6-disubstituted fulvenes so that the resulting bridging group is a tertiary carbon atom.

The fulvenes useful in preparing the ligands of the present invention have substituents in the 3 and 4 positions Q and are generally 6,6 disubstituted, while the other sites can be substituted or unsubstituted as shown below:

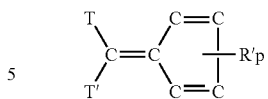

where R'p is the substituent on the resulting Cp ring and where the T, T' and the exocyclic carbon (C6 in fulvene) are the precursors of the structural bridging group R".

As noted previously, a preferred method of converting the neutral metallocenes to cationic metallocenes useful in the present invention involves reaction of the neutral metallocenes with a triphenylcarbenium boronate. A preferred reactant is triphenylcarbenium tetrakis(pentafluorophenyl) boronate.

The catalysts of the present invention can also be used to prepare pre-polymerized catalysts according to methods known in the art, such as the one disclosed in U.S. Pat. Nos. 3,893,989, 4,200,171, 4,287,328, 4,316,966 and 5,122,583. The pre-polymerized catalysts can be prepared in the presence of cocatalysts, such as the ones described previously and optionally in the presence of various electron donors.

Preferred pre-polymerized metallocenes of the present invention have a weight ratio of polymer/metallocene of approximately 0.1–100; ratios of less than 10 are particularly preferred. The syntheses are conveniently done at room temperature or lower in low boiling solvents which are readily evaporated in vacuo.

Experimental Part

PPA means polyphosphoric acid, the synthesis of which is described in F. D. Popp and W. E. McEwen, Chem. Rev., 58, 321 (1958); F. Uhlig and H. R. Snyder, Advances in Organic Chemistry, 1, 35 (1960).

EXAMPLE 1

Synthesis of bis(2-methylthiapentenyl)zirconium dichloride a. Synthesis of 4,5-Dihydro-5-methyl-6H cyclopenta(b)thiphene-6-one

[The following is a modification of the procedure originally described by O. Meth-Cohn, S. Gronowitz, *Acta Chemica Scandinavica*, 20 (1966) 1577–1587.]

A solution containing thiophene (65.7 g. 781 mmol), methacrylic acid (66.56 g. 773 mmol), and methylene chloride (50 mL) were added dropwise to a solution of PPA (prepared above) over a 1 h. period, while maintaining the temperature at 50° C. The reaction mixture was stirred an additional 2 h. then poured onto 1 L of ice (prepared in a 2 L sep.funnel), and the organic layer collected with methylene chloride in hexane solution (30%, 100 mL) The organic layer was then washed with water (250 mL), a saturated solution of sodium bicarbonate (2×250 mL), followed by water (2×250 mL). The organic layer collected in this fashion was then dried over magnesium sulfate, filtered and dried in vacuo yielding 93.5 g of a dark brown, slightly viscous oil. Further distillation of this material produced 52.2 g (1 mmbar, 92° C.–98° C.) of the target material. Yield=44%. 1H NMR: $CDCl_3$ ppm; 7.85 (d, 1H), 6.95 (d, 1H), 2.4–3.3 (m, 2H), 1.25 (d, 3H).

b. Synthesis of the 5-methyl-1-thiapentalenyl hydrazine

[The following is a modification of the procedure originally described by Hendrich Volz and Henrich Kowarsch, *Tet. Lett.,* 48 (1976) 4375].

Absolute ethanol (300 g) was treated with a vigorous stream of gaseous hydrochloric acid until saturated. Toluene-4-sulfono hydrazine (64 g. 343 mmol) was added as a dry powder, forming a white slurry. 4,5-Dibydro-5-methyl-6H-cyclopenta(b)thiphene-6-one (52.2 g. 343 mmol) was added dropwise over a 30 minute period. The solution turned to a clear, straw colored liquid, then formed a white precipitate which was collected by filtration. The precipitate was washed with THF (800 mL) then dried in vacuo. Yield: 100 g (91.5%).

c. Synthesis of 5-methyl-1-thipentalene 5-methyl-1-thiapentalenyl hydrazine (12.8 g. 40 mmol) was slurried in diethylether (100 mL) and the temperature lowered to −78° C. Methyllithium (100 mmol, 1.6 M solution in diethylether, 62.5 mL) was added dropwise. The temperature was allowed to rise to ambient stirring was continued for 16 h with the color turning deep purple. A deoxygenated saturated aqueous ammonium chloride solution was added dropwise (2 mL) and stirred for an additional 15 minutes, the color of the solution turning yellow. The slurry was then filtered through a medium porosity frit and the solids were washed repeatedly with fresh diethylether (250 mL). The diethylether in the filtrate was then removed in vacuo and a dark brown oil recovered (1.62 g. 30%). Mass spectrum (typical, first isomer; m/e (RA) 136 (11.4), 134 (100), 121 (25), 77 (12).

d. Synthesis of bis(2-methylthiapentenyl)zirconium dichloride Zirconium tetrachloride (800 mg, 3.4 mmol) was added as a dry powder to 5-methyl-1-thiapentalenyl lithium salt (400 mg, 3.6 mmol) and pentane (50 mL) and THF (5 mL) were added to make a slurry. The slurry was stirred an additional 16 h. after which time the solvents were removed in vacuo and a bright yellow free flowing powder was recovered (1 g). Sample was used for polymerization without further purification. 1H-NMR (THF-d8): ppm, 7.4 (m, 1H), 7.0 (m, 1H), 5.9 (s, 1.5H), 5.7 (s, 1H), 2.1 (s, 3H).

EXAMPLE 2

Ethylene Polymerization with bis(2-methylthiapentenyl)zirconium dichloride

Ethylene polymerizations were run in a 500 mL glass reactor with indirectly coupled magnetic stirring. Catalyst (20 mg) was added to a 10 mL glass vial and MAO was added (2.5 mL, 10 wt % in toluene). An additional 2.5 mL was added to the toluene solution used as the polymerization solvent. The solution containing the catalyst/MAO was added to the reactor containing the toluene/MAO via cannula. The reactor was purged of any residual nitrogen and replaced with ethylene. Ethylene was added to the reactor and the pressure was maintained at 3 bar for 8 minutes after which time the reaction was quenched with 5 mL of distilled water. The reactor contents were then poured into a deashing solution containing HCI (4 N, 120 mL) and methanol (80 mL). The organic layer was dried in vacuo under mild heat (50° C., 3 h).

Yield: 2.5 g; [η]THN=3.47 (dl/g).

EXAMPLE 3

Propylene Polymerization with bis(2-methylthiapentenyl) zirconium dichloride

Propylene polymerizations were run in a 500 mL glass reactor with indirectly coupled magnetic stirring. Catalyst (20 mg) was added to a 10 mL glass vial and MAO was added (5.0 mL, 10 wt % in toluene). The reactor was purged of any residual nitrogen and replaced with propylene. Propylene was added to the reactor and the pressure was maintained at 3 bar for 60 minutes after which time the reaction was quenched with 5 mL of distilled water. The reactor contents were then poured into a deashing solution containing 120 mL 4N HCI and 80 mL methanol. The organic layer was dried in vacuo under mild heat (70° C., 1 h).

Yield: 13.5 g viscous oil. [η]THN=0.18 (dl/g).

EXAMPLE 4

Synthesis of dimethylsilylbis(2-methylthiapentenyl)zirconium dichloride a. preparation of 5-methyl-1-thiapentalene:

The synthesis was carried out according to above described Example 1c.

b. Synthesis of dimethylsilylbis(2-methylthiapentenyl):

5-methyl-1-thipentalene (1.62 g. 11.9 mmol) was dissolved in 30 mL of diethylether and the temperature lowered to −78° C. Methyllithium (11.9 mmol, 1.6M of a diethylether solution, 7.4 mL), was added dropwise. The flask and contents were allowed to warm to room temperature and stirring was continued for 3 h. In a separate flask, dimethyldichlorosilane (0.77 g. 5.9 mmol, 0.78 mL) was dissolved in 20 mL of THF and the temperature lowered to −78° C. The slurry containing the 5-methyl-1-thipentalene anion was added dropwise to the stirred solution. The flask and contents were then allowed to warm to room temperature. A sample was taken for analysis, quenched with saturated solution of aqueous ammonium chloride, dried over magnesium sulfate, filtered, concentrated in vacuo, then submitted for analysis (20549-47C, 37.6% purity by GCMS). Mass spectrum (m/e (RA): 328 (18.7), 193 (100), 165 (29.1), 159 (36.7), 134 (53.4), 91 (81.2), 59 (27.7), 43 (10.5).

c. Synthesis of dimethylsilylbis(2-methylthiapentenyl)zirconium dichloride

A solution containing dimethylsilylbis(2-methylthiapentenyl) (1.78 g. 5.95 mmol) in diethylether (prepared above) at −78° C. was treated with methyllithium (11.9 mmol, 1.6M solution in diethylether, 7.4 mL). The contents were allowed to warm to room temperature and stirring was continued for 16 h. Solvents were removed in vacuo and the solids were washed repeatedly with fresh pentane (3×30 mL). Zirconium tetrachloride was added as a dry powder, and pentane was added. Pentane was then evaporated and replaced with toluene and the solution was stirred overnight. The solids were filtered and the filtrate dried in vacuo. Yield: 1.49 g (54%).

EXAMPLE 5

Propylene Polymerization with dimethylsilylbis(2-methylthiapentenyl)zirconium dichloride Propylene polymerizations were run in a 500 mL glass reactor with indirectly coupled magnetic stirring. Catalyst (20 mg) was added to a 10 mL glass vial and MAO was added (5.0 mL, 10 wt % in toluene). The reactor was purged of any residual nitrogen and replaced with propylene. Propylene was added to the reactor and the pressure was maintained at 3 bar for 60 minutes after which time the reaction was quenched with 5 mL of distilled water. The reactor contents were then poured into a deashing solution containing 120 mL 4N HCl and 80 mL methanol. The organic layer was dried in vacuo under mild heat (700 C, I h).

Yield: 19.6 g white free flowing polymer, [η]THN=0.49 (dl/g).

EXAMPLE 6

Synthesis of isopropylidene[cyclopentadienyl-(7-cyclopenadithiophene)]zirconium dichloride a. Synthesis of 7H-cyclopenta[1.2-b: 4.3-b']dithiophene 7H-cyclopenta[1.2-b: 4.3-b']dithiophene (referred to in the following examples as cyclopentadithiophene) was synthesized according to the procedure originally described by A. Kraak et al, Tetrahedron, 1968, 24, 3381–3398.

b. Isopropylidene(7H-cyclopentadithiophene)(cyclopentadiene).

A solution of cyclopentadithiophene (1.0 g. 5.62 mmol) in ether (15 mL) was cooled to −78 C and treated with n-butyllithium (5.75 mmol, 2.3 mL of 2.5 M solution in hexanes,). After stirring at 0° C. for 2 h. a solution of 6,6-dimethylfulvene (0.60 g, 5.62 mmol) in ether (5 mL) was added over a 30 minute period. The temperature was held at 0° C. for 1 h and then the contents were warmed to 25 C and stirred for 16 h. The reaction was stopped by adding a solution of saturated $NH_4Cl$ (15 mL). The organic layer was separated, washed with saturated salt solution (2×15 mL), and dried over $MgSO_4$. After filtration, solvents were removed by rotoevaporation to an oily residue. The product was crystallized from a mixture of methanol/acetone as a white solid (700 mg, 44%). Proton NMR ($CDCl_3$) ppm: (2 isomers) 7.23 (d. 2H), 7.10 (d. 2H), 6.1–6.8 (m, 3H), 3.1 (m, 2H), 1.18, 1.29 (2s, 6H). Mass spectrum: C17H16S2 PM=284.

c. Isopropylidene[cyclopentadienyl-(7-cyclopenatadithiophene)]zirconium dichloride.

A solution of isopropylidene(7H-cyclopentadithiophene) (cyclopentadiene) (540 mg, 1.9 mmol) in THF (20 mL) was cooled to −78 C and treated with n-butyllithium (4.0 mmol, 1.6 mL of 2.5 M solution in hexanes). The reaction contents were slowly warmed to O C and stirring continued for 4 h giving a dark red solution. Solvents were removed in vacuo at 0° C. and the residue was reslurried in ether (15 mL) at −78 C. $ZrCl_4$ (0.443 g. 1.9 mmol) was added as a slurry in pentane (10 mL) by cannula and the reaction contents were slowly warmed to room temperature while stirring for 16 h. The precipitated crude product was collected on a closed frit, washed with ether and pentane and dried in vacuo (yield: 1.0 g). A sample of the title compound used in polymerization tests was obtained by extraction with toluene at 50° C.

Proton NMR ($CD_2Cl_2$) ppm, δ, 7.42 (d, 2H), 7.21 (d, 2H), 6.44 (t, 2H), 5.84 (t, 2H), 2.05 (s, 6H).

EXAMPLE 7

Ethylene Polymerization with isopropylidene[cyclopentadienyl-(7-cyclopentadithiophene)]zirconium dichloride Ethylene polymerizations were run in a 500 mL glass reactor with indirectly coupled magnetic stirring. Catalyst (10 mg) was added to a 10 mL glass vial and MAO was added (2.5 mL, 10 wt % in toluene). An additional 2.5 mL was added to the toluene solution used as the polymerization solvent. The solution containing the catalyst/MAO was added to the reactor containing the toluene/MAO via cannula. The reactor was purged of any residual nitrogen and replaced with ethylene. Ethylene was added to the reactor and the pressure was maintained at 3 bar for 8 minutes after which time the reaction was quenched with 5 mL of distilled water. The reactor contents were then poured into a deashing solution containing HCl (4 N, 120 mL) and methanol (80 mL). The organic layer was washed with water and polymer solids were collected by filtration and washed with fresh methanol. The polymer was dried in vacuo under mild heat (50° C., 3 h).

Yield: 4.3 g; I.V. (THN)=3.7 (dl/g).

EXAMPLE 8

Propylene Polymerization with isopropylidene [cyclopentadienyl-(7-cyclopentadithiophene)]zirconium dichloride Propylene polymerizations were run in a 500 mL glass reactor with indirectly coupled magnetic stirring. Catalyst (20 mg) was added to a 10 mL glass vial and MAO was added (5.0 mL, 10 wt % in toluene). The reactor was purged of any residual nitrogen and replaced with propylene. Propylene was added to the reactor and the pressure was maintained at 3 bar for 60 minutes after which time the reaction was quenched with 5 mL of distilled water. The reactor contents were then poured into a deashing solution containing 120 mL 4N MCI and 80 mL methanol. The organic layer was washed with water and solvents removed on a rotoevaporator. The viscous polymer was dried in vacuo under mild heat (50 C, 1 h) Yield: 30 g polymer, I.V. (THN)=0.30 (dl/g).

EXAMPLE 9

Synthesis of isopropylidene[(t-butylcyclopentadienyl)-(7-cyclopentadithiophene)]zirconium dichloride a. Synthesis of 7H-cyclopenta[1.2-b: 4.3-b']dithiophene 7H-cyclopenta[1.2-b: 4.3-b']dithiophene (referred to in the following examples as cyclopentadithiophene) was synthesized according to the procedure originally described by A. Kraak et al, Tetrahedron, 1968, 24, 3381–3398.

b. preparation of 3-t-butyl-6,6-dimethylfulvene

Dry acetone (99.3 mmol, 5.77 g, 7.3 mL) and t-butylcyclopentadiene (50.6 mmol, 6.17 g) were mixed in a dropping funnel and added at room temperature to an ethanol solution (10 mL) of KOH (10.3 mmol, 0.58 g) stirring under nitrogen. After stirring overnight, the golden solution was diluted with ether, washed with 2 N HCl, water, and dried over sodium sulfate. A sample of the crude organic fraction (7.4 g) was taken for analysis (GCMS) showing 90% conversion to the title compound. The product was submitted to distillation. $^1$H-NMR (CDCl$_3$): δ 1.38 (s, 9H), 2.28 (s, 6H), 6.24 (m, 1H), 6.63 (m, 2H).

c. synthesis of isopropylidene(3-t-butylcyclopentadienyl) (7H-cyclopentadithiophene).

A solution of cyclopentadithiophene (4.9 mmol, 0.87 g) in dry ether was cooled to −78° C. and treated with n-butyllithium (4.9 mmol, 1.95 mL of 2.5 M solution in hexane). The reaction mixture was warmed to 0° C. and stirred for 4 h. A solution of 3-t-butyl-6,6-dimethylfulvene (4.9 mmol, 0.79 g) in ether (10 mL) was added dropwise, stirred for 2 h at 0° C., and then at room temperature for 16 h. The reaction was quenched by slow addition of a saturated solution of NH$_4$Cl (10 mL). The aqueous layer was separated, washed with ether and discarded. The organic fractions were combined, dried over MgSO$_4$, filtered, and evaporated to an oil. The oil was redissolved in a mixture of methanol/acetone and the product was crystallized by cooling on dry ice. Yield: 800 mg, 48%.

d. Isopropylidene [t-butylcyclopentadienyl-(7-cyclopentadithiophene)]zirconium dichloride Isopropylidene[t-butylcyclopentadienyl-(7-cyclopentadithiophene)] (800 mg, 2.4 mmol) was dissolved in THF (20 mL). The temperature was lowered to −78° C. and n-butyllithium (4.8 mmol, 1.92 mL of a 2.5 M solution in hexane) was added dropwise. The solution turned dark brown, was stirred an additional 10 minutes at −78° C., and allowed to slowly rise to ambient temperature. After gas evolution had stopped (2 h) stirring continued for 1 h before. THF was removed under pressure. The solids were washed with pentane and dried in vacuo. ZrCl$_4$ (2.5 mmol, 0.56 g) was added and the mixture of solids were suspended in pentane (50 mL) and stirred for 16 h. Then, pentane was decanted off and the product dried in vacuo yielding 1.21 g of a light brown free flowing powder. The product (1.2 g) was slurried in 30 mL Me$_2$Cl$_2$. After filtering and drying in vacuo 150 mg of the complex was isolated. $^1$H-NMR ppm: δ 7.40 (d, 2H), 7.22 (m, 2H), 6.30 (t, 1H), 5.85 (t, 1H), 5.65 (t, 1H), 2.0 (s, 6H), 1.2 (s, 9H).

EXAMPLE 10

Propylene Polymerization with isopropylidene[t-butylcyclopentadienyl-(7-cyclopentadithiophene)]zirconium dichloride Propylene polymerizations were run in a 250 mL glass reactor with indirect coupled magnetic stirring, internal temperature probe, and external temperature bath. The reactor was charged with toluene (100 mL) and MAO (3 mL, 10 wt/% solution in toluene from Witco Corp., 4.7 wt % Al). The contents was thermostated at 50° C. under stirring. The desired amount of a calibrated metallocene/toluene solution was added and stirred for 5 minutes. Propene gas was added to the desired pressure. Monomer pressure and temperature were kept constant during the run. The reaction was stopped after 1 h by venting the pressure and adding 5 mL of acidified methanol. The contents of the reactor were quantitatively transferred into an acidified methanol solution under vigorous stirring for several minutes before separating the organic fraction. After thorough washing with water, solvents were removed by rotoevaporation. The polymer was dried in vacuo under mild heat. Yield: 28 g polymer. I.V. 0,3 dl/g; mp.: 128° C.; mrrm: 2.9 mol %.

EXAMPLE 11

Synthesis of bis(4-phenyl-2,6-dimethyl-thiopentalene)zirconium dichloride a. Preparation of 3,4-bischloromethyl-2,5-dimethylthiophene In a 2 L round bottom flask equipped with 100 ml dropping funnel and mechanical stirring was added 2,5-dimethylthiophene (253.6 g, 2.26 mmol) and HCl (41.3 g, 1.13 mol, 94.5 mL of a 37 wt % solution). HCl gas was added in a slow stream for 5 minutes prior to the dropwise addition of a solution containing (aqueous) formaldehyde (69.1 g, 2.3 mol, 172 mL of a 37 wt % solution). The temperature was maintained between −15° C. and 0° C. during the course of addition (1 h 20 min). After completion of the addition, the contents was stirred an addition 1 h. The reaction mixture was quenched with H2O (400 mL), and the organic layer collected with diethylether (400 mL). The organic layer was washed with a saturated solution containing Na2CO3, water, dried over magnesium sulfate, filtered, then the solvents were removed in vacuo to yield 349.0 g of reaction product. Further purification by vacuum fractional distillation at 190 mtorr yields to 60.54 of the desired product.

b. Synthesis of 4-phenyl-2,6-dimethyl-thiopentalene-4-ol

In a 2 L round bottom flask with mechanical stirring was added magnesium powder (29 g, 1.2 mol) and covered with THF (20 mL). Then the turnings were activated with 5 crystals of iodine and dibromoethane (1.5 mL). After activation was complete, THF was removed and replaced with fresh THF. A solution containing 3,4-bis-chloromethylthiophene (42.8 g, 205 mmol) in THF (1 L) was added dropwise and stirred for additional 18 h. A solution containing Methylbenzoat (29 g, 213 mmol) dissolved in THF (220 mL) was added dropwise to the rapidly stirred solution and the mixture was stirred an additional 5 h. The reaction mixture was then quenched by adding a mixture of THF/water, then H2O (200 mL) was added and the organic fraction was collected with dry diethylether. The organic layer was then dried over MgSO4, filtered, and the solvents were removed under vacuum to yield 61.9 g of a bright orange oil, containing 57% of the desired product. (71% isolated yield).

c. Synthesis of 4-phenyl-2,6-dimethyl-thiopentalene

In a 2 L round bottom flask with reflux condenser was placed the alcohol to be dehydrated (45.9 g) was dissolved in toluene (100 mL). Paratoluensulfonic acid monohydrate (1.6 g) and 1 g Amberlite IR-120 were added. The contents were heated to reflux for 4 h, then the flask and the contents were allowed to cool to room temperature. The organic layer was collected, washed repeatedly with H2O, dried over MgSO4. After filtration, the solvent was removed by rotoevaporation to yield 41.45 g of a dark brown oil.

d. Synthesis of bis(4-phenyl-2,6-dimethylthiopentalene)zirconium dichloride

In a 100 mL round bottom flask with stirring bar and sidearm was added a 80% mixture (2.8 g, 10 mmol) containing 4-phenyl-2,6-dimethyl-3-ene(b)thiophene. The complex was dissolved in dry diethylether (50 mL), then n-butyllithium (12.5 mmol, 5 mL of a 2.5 M solution) was added dropwise at room temperature. The mixture was stirred for 1 h forming a bright orange solid precipitate which was collected by removing the solvent in vacuo. Zirconium tetrachloride (1.16 g, 5 mmol) was added and the solids were suspended in pentane (50 mL). The reaction mixture was stirred for 18 h, then the solids were collected by filtration, washed with fresh pentane, and dried in vacuo. A portion of the solids collected in this fashion were dissolved in toluene, then filtered. The toluene was removed in vacuo and 1.38 g of a dark red glassy free flowing solid was collected. 1H-NMR: δ ppm: 7.25 (m, 10H), 5.78 (s, 4H), 2.44 (s, 6H).

EXAMPLE 12

Propylene Polymerization with bis(4-phenyl-2,6-dimethylthiopentalene)zirconium dichloride A 250 mL glass reactor bottle was charged with 100 mL toluene. A solution containing bis(4-phenyl-2,6-dimethylthiopentalene)zirconium dichloride (5 mg), and MAO (5 mL, 10 wt % in toluene) was added. The reactor was sealed and the pressure was raised to 4 bar with propylene gas. Temperature was controlled at 40° C. during the polymerization. After 1 h, the reactor was purged with nitrogen and the solution quenched with an aqueous solution containing 30% (v/v) HCl (37 wt %) and 30% methanol. After filtration of the toluene soluble material, the solvent was removed in vacuo. Yield: 300 mg polymer.

% m=75.4; η=512 (by NMR).

EXAMPLE 13

Preparation of dimethylsilylbis(1-phenyl-2,5-dimethyl-1-azapentalene-4-yl)zirconium dichloride a. Synthesis of 1-phenyl-2-methylpyrrole I Butyllithium (0.700 mol, 280 mL of 2.5 M solution in hexane) was added slowly at room temperature to a mixture of 1-phenylpyrrole (0.695 mol, 100 g) and TMEDA (0.700 mol, 106 mL) in hexane (80 mL) and stirred for 3 h. The slurry was diluted with 300 mL of THF and iodomethane (0.771 mol, 48 mL) was added slowly maintaining the temperature between 35–40° C. After stirring at room temperature for 16 h, 250 mL of water were added and the organic layer was separated. The aqueous layer was extracted with ether (2×100 mL) and the combined organic fractions were dried over MgSO$_4$. After filtration, evaporation of solvents and TMEDA yielded 107 g of light brown oil (98% yield, +95% purity by GC). $^1$H-NMR δ (CDCL$_3$): 7.29–7.44 (m, 5H), 6.80 (m, 1H), 6.23 (m, 1H), 6.08 (m, 1H), 2.24 (s, 3H).

b. Synthesis of 1-phenyl-5-methyl-2-pyrrolecarboxaldehyde II

POCl$_3$ (0.375 mol, 35 mL) was added dropwise to 37 mL of DMF and stirred for 10 min. The temperature was lowered to 0° C. and a mixture of I (55 g, ca. 0.340 mol) and DMF (7 mL) was added dropwise. The viscous solution was slowly warmed to 50° C. and stirred for 1 h. After cooling to room temperature, the flask was opened to the air and charged with 350 g of crushed ice. A 20 wt % solution of NaOH (430 mL) was added cautiously and the mixture was immediately heated to 90–95° C. and stirred for 10 min. The flask was placed in an ice bath and the product solidified upon cooling. The solids were collected on a filter funnel, washed with water, redissolved in dichloromethane, and dried over MgSO$_4$. After filtration, evaporation of the solvent yielded 38 g of light brown solids (60% yield). $^1$H-NMR showed the crude product to be a mixture of 1-phenyl-5-methyl-2-pyrrolecarboxaldehyde and 1-phenyl-2-methyl-3-pyrrolecarboxaldehyde in ca. 4:1 ratio. Spectroscopically pure 1-phenyl-5-methyl-2-pyrrolecarboxaldehyde was obtained by recrystallization from ether.

The assignment of the two isomers was confirmed by NOESY NMR experiment.

$^1$H-NMR δ (CDCL$_3$) of 1-phenyl-5-methyl-2-pyrrolecarboxaldehyde: 9.26 (s, 1H, Py-COH), 7.43 (m, 3H, ArH), 7.22 (m, 2H, ArH), 7.00 (d, 1H, PyH), 6.12 (d, 1H, PyH), 2.04 (s, 3H, PyCH$_3$), mp 85° C. $^1$H-NMR δ (CDCL$_3$) of 1-phenyl-2-methyl-3-pyrrolecarboxaldehyde: 9.88 (s, 1H, PyCOH), 7.43 (m, 3H, ArH), 7.22 (m, 2H, ArH), 6.68 (d, 1H, PyH), 6.62 (d, 1H, PyH), 2.39 (s, 3H, PyCH$_3$).

c. Synthesis of Ethyl β-(1-phenyl-2-methylpyrrol-5-yl) methacrylate (III)

Triethyl 2-phosphonopropionate (93.3 mmol, 20 mL) was diluted with THF (15 mL) and added slowly to NaH (130 mmol, 3.16 g) in THF (40 mL) at 0° C. Stirring was continued at room temperature for 30 min. after gas evolution had ceased. The temperature was lowered to −10° C. and a solution of (II) (86.5 mmol, 16.0 g) in 50 mL THF was added dropwise. The flask and contents were warmed to room temperature over a 30 min. period resulting in a thick precipitate which decoupled the magnetic stirrer. A saturated solution of NH$_4$Cl (50 mL) was added cautiously dissolving the precipitate. After evaporating THF, the crude product was extracted with ether (2×100 mL), washed with brine solution, dried over MgSO$_4$, filtered and evaporated to a brown oil. Yield: 22.5 g (96.5%) of spectroscopically pure product. $^1$H-NMR (CDCl$_3$): 7.41 (m, 3H, ArH), 7.15 (m, 3H, ArH (2 H's)+PyCHC(CH$_3$) (CO$_2$Et)), 6.60 (d, 1H, PyH), 6.12 (d, 1H, PyH), 4.04 (q, 2H, OCH$_2$CH$_3$), 2.09 (s, 3H, PyCHC(CH$_3$)(CO$_2$Et)), 2.00 (s, 3H, PyCH$_3$), 1.12 (t, 3H, OCH$_2$CH$_3$).

d. Synthesis of Ethyl β-(1-phenyl-2-methylpyrrol-5-yl) isobutyrate (IV)

A solution of (III) (10 g, 37 mmol) in ethanol (50 mL) was stirred under 3.5 bar of hydrogen pressure at room temperature with 300 mg of 10% Pd on carbon for 1 h. Evaporation of the filtered golden solution gave ethyl β-(1-phenyl-2-methylpyrrol-5-yl)isobutyrate as a yellow syrup (9.4 g, 95% pure by GC). $^1$H-NMR δ (CDCl$_3$): 7.43 (m, 3H, ArH), 7.23 (m, 2H, ArH), 5.92 (m, 2H, PyH), 4.00 (q, 2H, OCH$_2$CH$_3$), 2.70 (m, 1H, PyCH$_2$CH(CH$_3$)(CO$_2$Et)), 2.46 (m, 2H, PyCH$_2$CH), 2.00 (s, 3H, PyCH$_3$), 1.21 (t, 3H, OCH$_2$CH$_3$), 1.05 (d, 3H, CH(CH$_3$)(CO$_2$Et)). ms (m/e) (rel intensity) 271 ([M$^+$], 23), 170 (100), 154 (12), 128 (6), 77 (10).

e. Synthesis of Ethyl β-(1-phenyl-2-methylpyrrol-5-yl) isobutyric acid (V)

A mixture of (IV) (9.4 g of crude oil, ca. 33 mmol) and Claisen's reagent (18 mL) were heated at 90–95° C. for 1 h. After cooling to room temperature, the solution was diluted with 15 g of crushed ice and acidified to pH 1–2 with 6 N HCl. The brown oily precipitate was dissolved in ether, washed with brine solution, dried over MgSO$_4$, filtered and evaporated to waxy solids. Triteration of the solids with pentane afforded 6.6 g of V as a tan powder (84.7% yield).

$^1$H-NMR δ (CDCl$_3$): 7.43 (m, 3H, ArH), 7.21 (m, 2H, ArH), 5.92 (m, 2H, PyH), 2.72 (dd, 1H, PyCH$_2$CH(CH$_3$) (CO$_2$Et)), 2.46 (m, 2H, PyCH$_2$CH), 2.00 (s, 3H, PyCH$_3$), 1.05 (d, 3H, PyCH$_2$CH(CH$_3$)).

f. Synthesis of 1-phenyl-5,6-dihydro-2,5-dimethylcyclopenta[b]azaphene-4-one (VI)

A solution of (V) (25 mmol, 6.0 g) in dichloroethane (45 mL) was added slowly to 100 g of 87% PPA at 85–90° C. and stirred for 3 h. The mixture was cooled to room temperature, 200 g of crushed ice were added, and stirring continued until all PPA had dissolved. The lower organic layer was separated and the aqueous layer was extracted with dichloromethane. The combined organic fractions were washed with $K_2CO_3$, brine solution, dried over $MgSO_4$, filtered and evaporated to an oil which solidified upon standing for 16 h. The solids were triterated with hexane/ether and dried under vacuum. Yield 2.85 g of white powder (51%). $^1$H-NMR δ (CDCl$_3$): 7.44 (m, 3H, ArH), 7.23 (m, 2H, ArH), 6.12 (s, 1H, PyH), 2.90 (m, 2H, PyCH$_2$), 2.32 (d, 1H, PyCH$_2$CH(CH$_3$)CO—), 2.09 (s, 3H, PyCH$_3$), 1.19 (d, 3H, PyCH$_2$CH(CH$_3$)CO—). ms (EI) (rel intensity): 223 ([M$^+$–2], 4), 205 (4), 149 (100), 121 (3), 104 (5), 93 (3), 76 (5). mp 106° C.

g. Synthesis of the Hydrazone of the Ketone (VII)

The ketone (VI) (31 mmol, 7.0 g), p-toluenesulfonhydrazide (36 mmol, 6.7 g), and p-toluenesulfonic acid monohydrate (6.3 mmol, 1.2 g) were dissolved in 50 mL of absolute ethanol and stirred at 65° C. for 24 h. After cooling to room temperature and standing for several hours, the precipitated product was collected on a filter funnel, washed with ether and dried under vacuum (yield 5.0 g) Solvents were removed from the filtrate and an additional 1.2 g of product were crystallized from an ether/toluene solution of the oily residue. Total yield: 6.2 g (51%) of light gray powder.

$^1$H-NMR δ (CDCl$_3$): 7.80 (d, 2H, ArH), 7.39 (m, 3H, ArH), 7.17 (m, 4H, ArH), 6.23 (s, 1H, PyH), 3.25 (tt, 1H, PyCH$_2$CH(CH$_3$)CN—), 2.89 (dd, 1H, PyCH$_2$), 2.35 (s, 3H, PyCH$_3$), 2.24 (dd, 1H, PyCH$_2$), 2.10 (s, 3H, Me), 1.15 (d, 3H, PyCH$_2$CH(CH$_3$)CN—). mp 156 ° C. (dec).

h. Synthesis of 1-phenyl-2,5-dimethyl-1-azapentalene (VIII)

The hydrazone (VII) (12.7 mmol, 5.0 g) was slurried in 20 mL of THF, cooled to 0° C., and treated with 2.1 eq of butyllithium (10.6 mL of 2.5 M BuLi in hexane). The mixture was slowly warmed to room temperature and an additional 10 mL of THF were added giving a dark solution. After 2 h, precipitates had formed and ether was added (ca. 30 mL) to further precipitate the product. The solids were collected on a closed filter funnel, washed with ether, and dried in vacuo (7.5 g). $^1$H-NMR of the crude product, protonated with wet CDCl$_3$, showed a mixture of two isomers. The solids were suspended in hexane (100 mL) and treated with a saturated solution of NH$_4$Cl. The hexane layer was separated, dried over MgSO$_4$, filtered and evaporated to an oil (1.0 g yield, 85% purity by GC/MS). Proton NMR of the oil showed a single isomer. $^1$H-NMR δ (CDCl$_3$): Isomer 1—7.33 (m, 5H, ArH), 5.96 (s, 1H), 5.86 (s, 1H) 3.15 (s, 2H, CH$_2$ of C$_5$ ring), 2.21 (s, 3H, PyCH$_3$), 2.04 (s, 3H, CH$_3$ at C-5). Isomer 2—7.33 (m, 5H, ArH), 6.11 (s, 1H), 5.85 (s, 1H), 3.15 (s, 2H, CH$_2$ of C$_5$ ring), 2.18 (s, 3H, PyCH$_3$), 2.00 (s, 3H, CH$_3$ at C-5). me (EI) (rel intensity): 209 (100), 194 (27), 167 (5), 117 (4), 91 (5), 77 (13).

(i) Synthesis of dimethylsilylbis(4-phenyl-2,5-dimethyl-4-azapentalene) (IX)

1-phenyl-2,5-dimethyl-1-azapentalene (7.18 mmol, 1.5 g) was dissolved in ether (40 mL), cooled to –78° C., and treated with 7.5 mmol of butyllithium (3 mL of a 2.5M solution in hexanes).

The solution was warmed to room temperature and stirred for 2 h. The precipitated lithium salt was collected on a closed filter funnel, washed with pentane, and dried in vacuo. The salt (700 mg) was redissolved in THF (40 mL), cooled to –78° C. and 0.2 mL (1.63 mmol) of dichlorodimethylsilane was injected with a gas tight syringe. The solution was heated to 55° C. and stirred for 16 h. Solvents were removed in vacuo and the crude product was used without further purification (The ligand was obtained as a mixture of isomers). $^1$H-NMR δ (CD$_2$Cl$_2$): 7.42–7.62 (m, 10H, ArH), 6.45, 6.42, 6.21, (3 s, 4H), 5.86 (s, 1H,) 3.62 (s, 2H), 2.48, 2.45, 2.43, 2.41 (4 s, 12H), –0.06, –0.08, –0.11 (3 s, 6H). $^{13}$C-NMR (CD$_2$Cl$_2$): 129.4, 126.4, 126.1 (Ar), 117.9, 104.6 (olefinic CH), 42.5 (CH), 18.0 (CH$_3$), 14.3 (CH$_3$), –7.1, –7.3, –7.6 (Si—CH$_3$). me (EI) (rel intensity): 474 (29), 266 (100), 251 (11), 208 (21), 192 (13), 77 (5).

(ii) Synthesis of dimethylsilylbis(4-phenyl-2,5-dimethyl-4-azapentalenyl)zirconium dichloride (X).

Product IX (1.1 g) was dissolved in ether (20 mL), cooled to –78° C., and treated with 4.8 mmol of butyllithium (1.9 mL of a 2.5M sol. in hexanes). The solution was warmed to room temperature and stirred for 16 h. The precipitated dianion was collected on a closed filter funnel, washed with pentane and dried in vacuo to a tan powder (0.7 g). The dianion was mixed with 0.32 g of ZrCl$_4$, cooled to –78° C., and treated with 20 mL of cold dichloromethane (–78° C.). The flask and contents were slowly warmed to room temperature, stirred for 4 h, and filtered. The filtrate was evaporated to a brown free flowing powder and used in polymerization tests without further purification.

EXAMPLE 14

Propylene polymerization with dimethylsilylbis(4-phenyl-2,5-dimethyl-4-azapentalene-4-yl)zirconium dichloride Propylene polymerizations were run in a 250 mL glass reactor with indirect coupled magnetic stirring, internal temperature probe, and external temperature bath. The reactor was charged with 100 mL of toluene. 10 mg of X in 5 mL of toluene were mixed with 3 mL of MAO (10 wt % solution in toluene from Witco Corp., 4.7 wt % Al) and charged to the reactor stirring at 25° C. The reactor was pressured to 4 bar with propylene and the temperature was raised to 50° C. The polymerization was stopped after 1 h by venting the pressure and injecting 5 mL of acidified methanol. The contents of the reactor were transferred into an acidified methanol solution under vigorous stirring for several minutes. After separating the organic fraction and washing with water, solvents were evaporated and the polymer was dried under vacuum and mild heat. Yield=15 g of free flowing powder (Mw=47,000, DSC melting point=153° C., $^{13}$C-NMR mrrm pentad=0.6 mol %).

EXAMPLE 15

Synthesis of dimethylsilyl(2-methylthiopentalene)(2-methylindene)zirconium dichloride a. Synthesis of dimethylsilyl(2-methylthiopentalene)chloride In a 500 mL round bottom flask equipped with sidearm, stirring bar, and 125 mL dropping funnel was added 31.9 g (100 mmol) of the asymmetric thiopentahydrazine dissolved in THF (70 mL). N-Butyllithium (250 mmol, 100 mL of a 2.5 M solution in hexane) was added dropwise. The reaction was stirred for an additional 5 h. after addition was complete. The reaction was then quenched with 250 mmol water (4.5 mL H$_2$O in 50 mL Et$_2$O). The organic layer was collected with Et$_2$O, dried over magnesium sulfate, filtered, then rotary evaporated to give a dark brown oil.

| Results: | area % |
|---|---|
| BTR | 7.6% |
| PM = 136 | 79.6% |
| ATR | 12.8% |

In a 250 mL round bottom flask with sidearm, stirring bar, and 60 mL dropping funnel was added the olefin (10 g, 73.5 mmol) prepared above, dissolved in THF (15 mL). N-Butyllithium (73.5 mmol, 29.4 mL of a 2.5 M solution in hexane) was added dropwise, and the reaction was stirred for 16 hours. Then the solvents were removed in vacuo and the solids were washed with pentane. In a separate 500 mL flask equipped with 125 mL dropping funnel was prepared dimethyldichlorosilane (19.3 g, 150 mmol, 18.2 mL, 1.5 eq.) dissolved in THF (30 mL). The anion prepared above was dissolved in THF (125 mL) and added dropwise to the silane solution. The reaction mixture was stirred 30 minutes after addition was complete, then the solvents were removed in vacuo. An orange oil with orange solids was recovered.

b. Synthesis of dimethylsilyl(2-methylindenyl)(2-methylthiopentalene)

In a 250 mL round bottom flask with sidearm, stirring bar, and 60 mL dropping funnel was added 2-methylindene (13 g, 100 mmol, product made by Boulder) dissolved in THF (20 mL). N-Butyllithium (100 mmol, 40 mL of a 1.6 M solution in hexane) was added dropwise at room temperature. After addition was complete, the flask and contents were stirred an additional 2 h. A solution containing dimethylsilyl(2-methylthiopentalene)chloride in THF (30 mL) was added dropwise at room temperature. Stirring was continued for 1 hour, after which time the reaction was quenched with 30 mL of a 30% water/THF mixture, concentrated on a rotary evaporated, and a sample submitted for analysis.

Results from GC of total reaction product:

| BTR | 0.7 | |
|---|---|---|
| PM = 130 | 61.9% | (2-methylindene starting material) |
| MTR | 1.6% | |
| PM = 322 | 31.7% | (target) |
| ATR | 4.1% | |

Mass spectrum (m/e(RA): 322 (34), 193 (100), 187 (37), 159 (37), 128 (26).

Further purification of this material was carried out by recrystallization from dichloromethane/MeOH. The solid material recovered in this fashion was then dried on the rotary evaporator. Results:

| BTR: | 0.7 |
|---|---|
| | (area %) |
| PM = 130 | 10.2 |
| MTR | 27.6 |
| PM = 322 | 48.5 |
| PM = 328 | 6.3 |
| ATR | 6.4 | c. Synthesis of dimethylsilyl(2-methylthiopentalene)(2-methylindene)zirconium dichloride In a 250 mL flask with sidearm and stirring bar was added the dimethylsilyl(2-methylindenyl)(2-methylthiopentalene) ligand (3.1 g, 9.6 mmol) dissolved in THF (70 mL). The temperature was reduced to −30° C. and n-butyllithium (20 mmol, 8 mL at 2.5 M in hexanes) was added dropwise. The reaction was stirred for 2 h after which time the solvent was removed in vacuo and the dianion collected in this fashion was washed with fresh pentane, then dried in vacuo. The dianion was taken into the dry-box and $ZrCl_4$ (2.23 g, 9.6 mmol) was added as a dry powder. The solids were then suspended in fresh pentane (70 mL) and stirred for 16 hours. Then the solvents were decanted and then the solids were dried in vacuo. The solids were then dissolved in dichloromethane and filtered. The dichloromethane was then removed in vacuo and the solids were washed with fresh pentane. The solids were again dried in vacuo, then dissolved in toluene and filtered. The toluene was removed in vacuo and 1.6 g of a dark brown free flowing solid was recovered.

EXAMPLE 16

Propylene Polymerization with dimethylsilyl(2-methylthiopentalene)(2-methylindene)zirconium dichloride In a 250 mL glass reactor was placed toluene (100 mL), catalyst (40 mg), and MAO (8 mL, 10 wt % in toluene). The reactor was sealed, then purged with propylene before raising the pressure to 4 bar. The polymerization reaction was controlled at 60° C. for 1 h. The reactor was then purged with nitrogen, and an acidic methanol solution was used to quench the reactor contents. The organic layer was collected, washed with water, then dried in vacuo. Yield: 38 g white non-sticky free flowing polymer.

In a 250 mL glass reactor was placed toluene (100 mL), catalyst (5 mg), and 5 mL MAO (10 wt % in toluene). The reactor was sealed, then purged with propylene before raising the pressure to 4 bar. The polymerization reaction was controlled at 60° C. for 1 h. The reactor was then purged with nitrogen, and an acidic methanol solution was used to quench the reactor contents. The organic layer was collected, washed with water, then dried in vacuo. Yield: 13 g white non-sticky free flowing polymer: % m=84.6, $M_n$=1132 (by NMR end group analysis).

EXAMPLE 17

Preparation of dimethylsilyl(2-methylthiopentalenyl)(1-phenyl-2,5-dimethyl-1-azapentylenyl)zirconium dichloride a. Preparation of thio(c)penta-4-methyl-5-dimethylsilylchloride In a 250 mL round bottom flask with sidearm, stirbar and 25 mL dropping funnel was places 6.18 g (45.4 mmol, 6 mL) of 2-methylthiopentalene (2-MeTp) dissolved in 30 mL diethylether. The temperature of the solution was reduced to −78° C. and 50 mmol n-butyllithium was added (20 mL, 2.5 M solution in hexane). The solution was warmed to room temperature, then stirred an additional 2 h. A yellow solid precipitate (anion, lithium salt of the 2-MeTp) was formed in the reaction flask, which was cooled to −78° C. A solution containing 11.7 g (91 mmol) dimethyldichlorosilane dissolved in 20 mL diethylether was added dropwise to the stirred reaction mixture. The flask and contents were allowed to warm to room temperature and stirred an additional 18 h. The crude reaction mixture was then filtered and the solvents were removed in vacuo producing a dark orange oil. Yield: 10.45 g: $^1$H-NMR CD$_2$Cl$_2$ (major isomer): s ppm: 7.2 (d,1H), 7.1 (d, 1H), 6.7 (m, 1H), 3.6 (s,1H), 2.3 (s,3H), 0.4 (s, 3H), 0.3 (s, 3H).

b. Preparation of dimethylsilyl(2-methylthiopentalene)(1-phenyl-2,5-dimethyl-1-azapentalene)

In a 250 mL round bottom flask with sidearm and stirbar was added 1.86 g (6.4 mmol) of the lithium salt of 1-phenyl-2,5-dimethyl-1-azapentalene (previously prepared), dissolved in 30 mL diethylether. A solution containing 1.46 g (6.4 mmol) thio(c)penta-4-methyl-5-dimethylsilylchloride dissolved in 30 mL diethyl ether was slowly added at room temperature and stirred an additional 48 h. The reaction was then quenched with a solution containing 10% water/THF, the organic layer was collected, dried over magnesium sulfate, filtered, then the solvents were removed in vacuo. Yield: 3.23 g of a dark brown oil: $^1$H-NMR CD$_2$Cl$_2$ (major isomer): s ppm: 7.5 (m, 5H), 7.28 (d, 1H), 7.1 (d, 1H), 7.0 (d, 1H), 6.9 (m, 1H), 5.9–6.3 (m, 1H), 3.0–3.3 (3s, 4H), 2.1–2.3 (m, 6H), 1.5 (s), 0.2 (m, 6H).

c. Preparation of dimethylsilyl(2-methylthiopentalenyl)(1-phenyl-2,5-dimethyl-1-azapentylenyl)zirconium dichloride In a 250 mL round bottom flask with sidearm and stirbar was added 2.8 g (7 mmol) dimethylsilyl(2-methylthiopentalene)(1-phenyl-2,5-dimethyl-1-azapentalene) ligand (prepared above) dissolved in 50 mL diethylether. Dropwise, n-butyllithium was added (14 mmol, 6 mL of a 2.5 M solution in hexane), and the crude reaction mixture was stirred an additional 2 h at room temperature. The solvent was then removed in vacuo and the remaining solids were washed with pentane. Zirconium tetrachloride (1.63 g, 7 mmol) was added as a solid, then the solids mixture was suspended in 70 mL fresh pentane. The contents of the reaction flask was stirred overnight. The solvents were evaporated, the solids collected in this fashion were suspended in toluene, filtered, and the toluene removed in vacuo to yield 660 mg of a light brown free flowing solid (mixture of isomers, rac/meso).

EXAMPLE 18

Propylene Polymerization with dimethylsilyl(2-methylthiopenta-yl)(1-phenyl-2,5-dimethyl-1-azapentylene-yl)zirconium dichloride In a 250 mL glass reactor was placed 100 mL toluene, 5 mg catalyst, and 5 mL MAO (10%). The reactor was sealed, then purged with propylene before raising the pressure to 4 bar. The polymerization reaction was controlled at 50° C. for 1 h. The reactor was then purged with nitrogen, and an acidic methanol solution was used to quench the reactor contents. The organic layer was collected, washed with water, then dried in vacuo. Result: 22.8 g polymer.

The invention claimed is:

1. A metallocene of formula (I):

wherein (1) Y is a coordinating group containing a six π electron central radical directly coordinating Me to which radical is fused one or more rings containing at least one non-carbon atom selected from B, N, O, Al, P, S, Ga, Ge, As, Se, In, Sn, Sb, and Te;

(2) R" is a divalent bridge between the Y and Z groups;

(3) Z is a coordinating group having the same meaning as Y or is an open pentadienyl containing group, a cyclopentadienyl containing group, a heterocyclopentadienyl containing group, a nitrogen containing group, a phosphorous containing group, an oxygen containing group, or a sulfur containing group;

(4) Me is an element belonging to Group 3, 4, 5, 6, or to the lanthanide or actinide series of the Periodic Table of the Elements;

(5) Q is a linear or branched, saturated or unsaturated alkyl radical, aryl radical, alkylaryl radical, arylalkyl radical, or a halogen atom;

(6) P is a stable non-coordinating or pseudo non-coordinating counterion;

(7) i is an integer having a value of 0 or 1;

(8) j is an integer having a value from 1 to 3;

(9) jj is an integer having a value from 0 to 2;

(10) k is an integer having a value from 1 to 3; and

(11) l is an integer having a value from 1 to 2.

2. A metallocene according to claim 1, wherein Y contains one heterocyclic ring fused to the central six π electron central radical.

3. A metallocene according to claim 2, wherein Y is a substituted cyclopentadienyl group of formula:

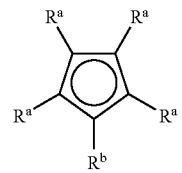

wherein the groups R$^a$, are identical or different from each other, are selected from the group consisting of hydrogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl radicals, and wherein at least two adjacent R$^a$ groups form a condensed heterocyclic C$_5$–C$_7$ ring containing at least one non-carbon atom selected from B, N, O, Al, P, S, Ga, Ge, As, Se, In, Sn, Sb, and Te;

R$^b$ is hydrogen, halogen, linear or branched, saturated or unsaturated, C$_1$–C$_{20}$ alkyl, C$_1$–C$_{20}$ alkoxyl, C$_6$–C$_{20}$-aryl, C$_7$–C$_{20}$ alkylaryl, C$_7$–C$_{20}$ arylalkyl C$_1$–C$_{20}$ acyloxyl group, optionally containing a silicon atom, or R$^b$ is the bridging divalent group R".

4. The metallocene according to claim 1, wherein Y contains at least two heteroatoms.

5. The metallocene according to claim 1, wherein i is 1, j is 1, and Z has the same meaning as Y.

6. A metallocene according to claim 1, wherein i is 1, j is 1, and Z is a cycolpentadienyl containing group, an open-pentadienyl containing group, a nitrogen containing group, a phosphorus containing group, an oxygen containing group, or a sulfur containing group.

7. A metallocene according to claim 1, wherein group Z is an open-pentadienyl containing group and it comprises a radical of formula (V):

where:

G is a carbon atom, a nitrogen atom, a silicon atom, or a phosphorus atom;

L is a $CR^3R^{3'}$ radical, a $SiR^3R^{3'}$ radical, a $NR^{3''}$ radical, a $PR^{3''}$ radical, an oxygen atom, or a sulfur atom;

L' is a $CR^4R^{4'}$ radical, a Si $R^4R^{4'}$ radical, a $NR^{4''}$ radical, a $PR^{4''}$ radical, an oxygen atom, or a sulfur atom;

$R^2$, $R^3$, $R^{3'}$, $R^{3''}$, $R^4$, $R^{4'}$, $R^{4''}$, and $R^5$, are the same or different from each other, can be hydrogen, a linear or branched $C_1$–$C_{20}$ hydrocarbon radical, a linear or branched, $C_1$–$C_{20}$ halocarbon radical, a $C_1$–$C_{20}$ hydrohalocarbon radical, a $C_1$–$C_{20}$ alkoxy radical, a $C_3$–$C_{12}$ cyclohydrocarbon radical, a $C_3$–$C_{12}$ cyclohydrohalocarbon radical, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical, or a halogen atom; $R^2$ and $R^3$, $R^{3'}$ or $R^{3''}$ and/or $R^5$ and $R^4$, $R^{4'}$ or $R^{4''}$ can form together a 4 to 6 membered ring or a 6 to 20 fused ring system; $R^3$, $R^{3'}$, or $R^{3''}$ and $R^4$, $R^{4'}$, or $R^{4''}$ can be joined together so that the five numbered atomic centers of the six π electron central radical are part of a 7 to 20 membered ring system.

8. A metallocene according to claim 1, wherein i is 1, j is 1, and ii is 1, and at least one β substituent on either Y or Z is a bulky group sterically larger than hydrogen or a fluorine atom.

9. A metallocene according to claim 1, wherein i is 1, j is 1, and where both Y and Z are bilaterally or pseudo-bilaterally symmetric and where Y or Z has at least one β substituent larger than hydrogen.

10. A metallocene according to claim 1, wherein i is 1, j is 1, and where one or both Y and Z are not bilaterally or pseudo-bilaterally symmetric, Y or Z having at least one β substituent larger than hydrogen.

11. A metallocene according to claim 10, having Cs or pseudo-Cs symmetry.

12. A ligand of formula (II):

wherein (1) Y is a coordinating group containing a six π electron central radical to which is fused one or more rings containing at least one non-carbon atom selected from B, N, O, Al, P, S, Ga, Ge, As, Se, In, Sn, Sb, and Te;
(2) R" is a divalent bridge between the Y and Z groups;
(3) Z is a coordinating group having the same meaning as Y or is an open pentadienyl containing group, a cyclopentadienyl containing group, a heterocyclopentadienyl containing group, a nitrogen containing group, a phosphorous containing group, an oxygen containing group, or a sulfur containing group;
(4) i is 1;
(5) j is an integer having a value from 1 to 3; and
(6) jj is 1.

13. A catalytic system for the polymerization of addition polymerizsable monomers, comprising the reaction product between:
(1) an heterocyclic metallocene as described in claim 1, and
(2) a suitable co-catalyst selected from the group consisting of trialkylaluminum, trialkyloxyaluminum, dialkylaluminum halides, alkylaluminum halides, and alumoxane.

14. A catalytic system according to claim 13, wherein the co-catalyst is an alumoxane.

15. A process for polymerizing addition polymerizable monomers, comprising contacting at least one catalytic system, as described in claim 13, with at least one addition polymerizable monomer.

16. A process according to claim 15, comprising contacting the metallocene contained in the catalytic system with a suitable co-catalyst, either prior to or after the metallocene is brought into contact with the monomer.

17. A process according to claim 15, comprising the following steps:

a) contacting the catalytic system with a small amount of the addition polymerizable monomer, to form a pre-polymerized catalyst; and
b) contacting the pre-polymerized catalyst obtained in step (a) with the addition polymerizable monomers.

18. A process according to claim 15, for the production of polyethylene, isotactic, syndiotactic, hemi-isotactic, atactic polypropylene, polyethylene copolymers, or polypropylene copolymers.

19. A metallocene according to claim 2, wherein Y is represented by the following formulae:

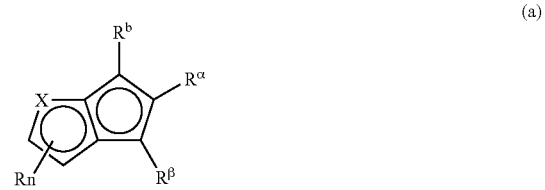

(a)

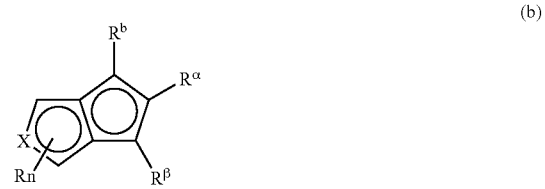

(b)

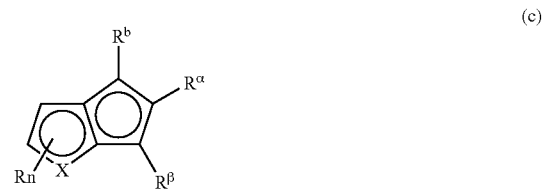

(c)

(d)

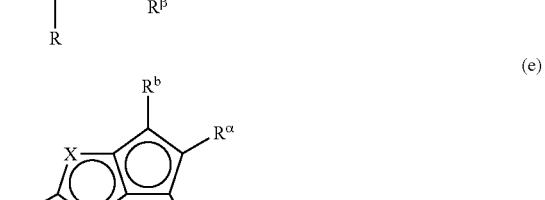

(e)

-continued
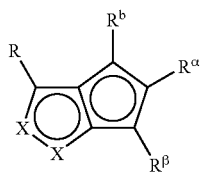
(f)
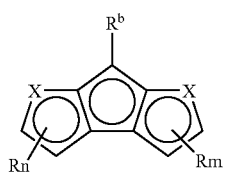
(g)
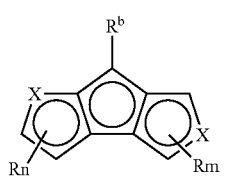
(h)
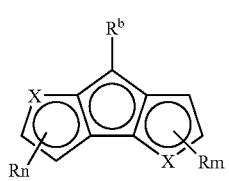
(i)
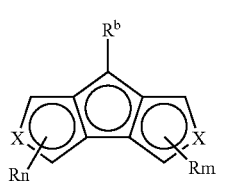
(j)
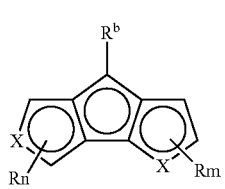
(k)
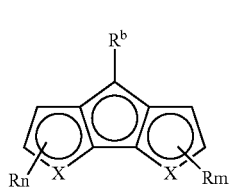
(l)
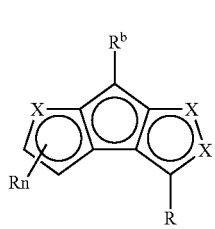
(m)
-continued
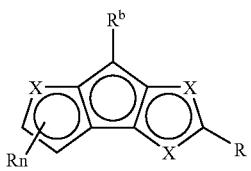
(n)
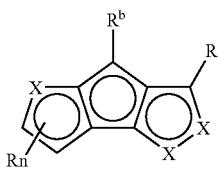
(o)
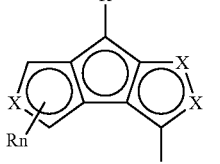
(p)
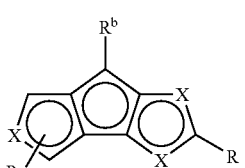
(q)
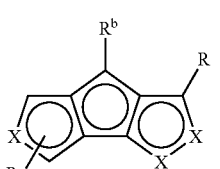
(r)
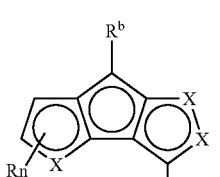
(s)
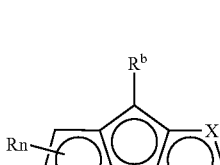
(t)
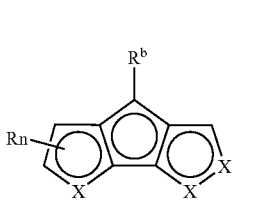
(u)

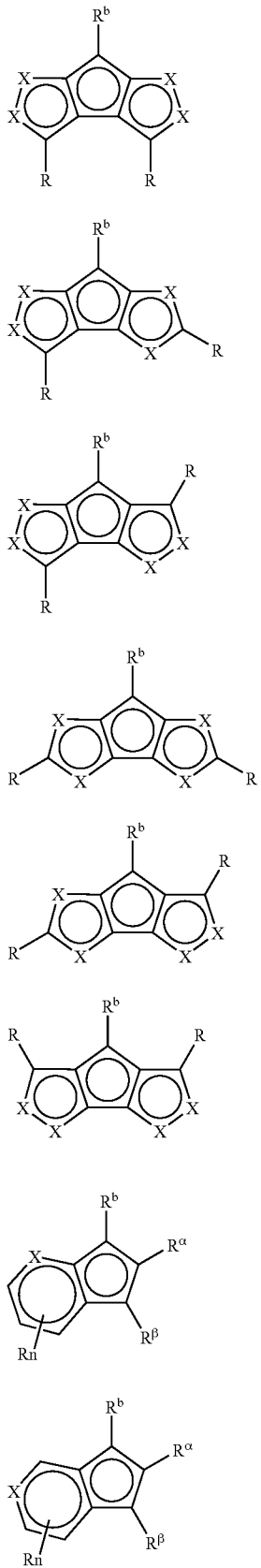

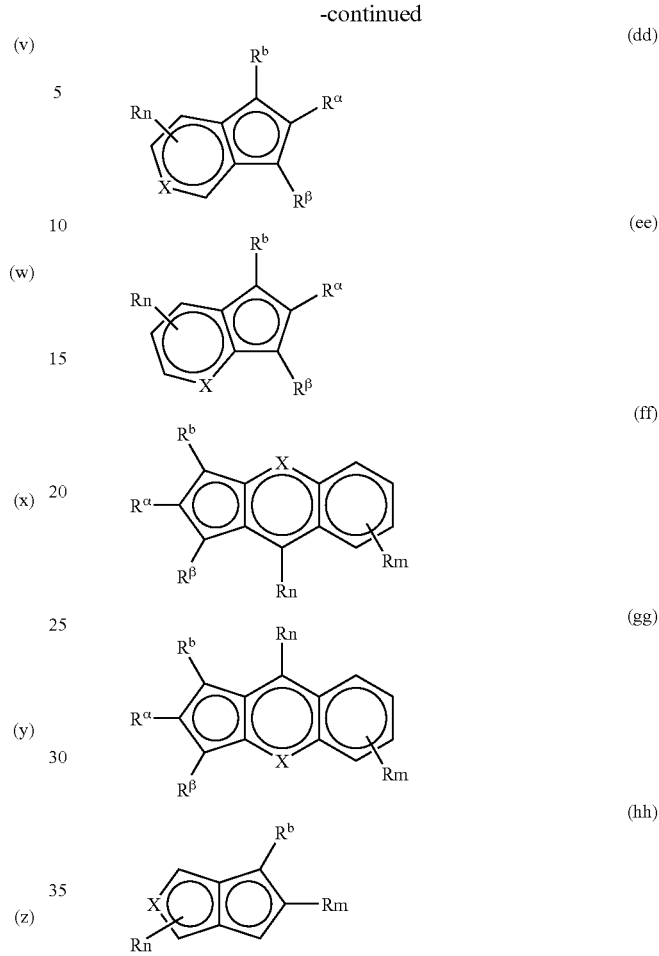

wherein:
(i) the X atoms are the same or different from each other, can be N, P, NR$^g$, PR$^g$, O or S; when a fused ring has two heteroatoms, then one X can be O or S the other X can be N, P, NR$^g$ or PR$^g$, or one can be N or P and the other can be NR$^g$ or PR$^g$, so that the molecular species represents a chemically viable group;

(ii) wherein R$^g$ a linear or branched $C_1$–$C_{20}$ hydrocarbon radical, optionally substituted with one or more halogen, hydroxy, alkoxy group, a $C_3$–$C_{12}$ cyclohydrocarbon radical, a $C_3$–$C_{12}$ cyclohydrohalocarbon radical, optionally substituted with one or more halogen, $C_6$–$C_{20}$ aryl radical, $C_7$–$C_{20}$ alkylaryl radical, $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical or a halogen atom;

(iii) the R groups, the same or different from each other, can be hydrogen, a linear or branched $C_1$–$C_{20}$ hydrocarbon radical, optionally substituted with one or more halogen, hydroxy, alkoxy, a $C_3$–$C_{12}$ cyclohydrohalocarbon radical, optionally substituted with one or more halogen, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical, or a halogen atom, two adjacent R groups can form together a saturated, unsaturated, or aromatic fused ring;

(iv) n and m are integers which have values from 0 to the maximum number of substituents that the ring can accommodate;

(v) $R^\alpha$ and $R^\beta$ representing α and β substituents respectively, are the same or different from each other, can be hydrogen, a linear or branched $C_1$–$C_{20}$ hydrocarbon radical, optionally substituted with one or more halogen, hydroxy, or alkoxy, a $C_3$–$C_{20}$ cyclohydrocarbon radical, optionally substituted with one or more halogens, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical, or a halogen atom; two adjacent $R^\alpha$ and $R^\beta$ groups can form together a saturated, unsaturated, or aromatic fused ring; and (vi) $R^b$ is a hydrogen, halogen, linear or branched, saturated or unsaturated, $C_1$–$C_{20}$ alkyl, $C_1$–$C_{20}$ alkoxyl, $C_6$–$C_{20}$ aryl, $C_7$–$C_{20}$ alkylaryl, $C_7$–$C_{20}$ arylalkyl, $C_1$–$C_{20}$ acyloxyl group, optionally containing a silicon atom, or $R^b$ is the bridging divalent group R".

20. A metallocene of formula (III):

$$Y_j R''_i Z_{jj} MeQ_k \qquad (III)$$

wherein (1) Y is a coordinating group containing a six π electron central radical directly coordinating Me to which radical is fused one or more rings containing at least one non-carbon atom selected from B, N, O, Al, P, S, Ga, Ge, As, Se, In, Sn, Sb, and Te;

(2) R" is a divalent bridge between the Y and Z groups;

(3) Z is a coordinating group having the same meaning as Y or is an open pentadienyl containing group, a cyclopentadienyl containing group, a heterocyclopentadienyl containing group, a nitrogen containing group, a phosphorous containing group, an oxygen containing group, or a sulfur containing group;

(4) Me is an element belonging to Group 3, 4, 5, 6, or to the lanthanide or actinide series of the Periodic Table of the Elements;

(5) Q is a linear or branched, saturated or unsaturated alkyl radical, aryl radical, alkylaryl radical, arylalkyl radical, or a halogen atom;

(6) i is an integer having a value of 0 or 1;

(7) j is an integer having a value from 1 to 3;

(8) jj is an integer having a value from 0 to 2; and (9) k is an integer having a value from 1 to 3.

21. A metallocene according to claim 20, wherein Y contains one heterocyclic ring fused to the central six π electron central radical.

22. A metallocene according to claim 21, wherein Y is a substituted cyclopentadienyl group of formula:

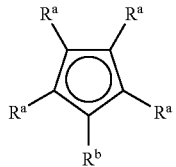

wherein the groups $R^a$, are identical or different from each other, are selected from the group consisting of hydrogen, linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl, and $C_7$–$C_{20}$ arylalkyl radicals, and wherein at least two adjacent $R^a$ groups form a condensed heterocyclic $C_5$–$C_7$ ring containing at least one non-carbon atom selected from B, N, O, Al, P, S, Ga, Ge, As, Se, In, Sn, Sb, and Te;

$R^b$ is hydrogen, halogen, linear or branched, saturated or unsaturated, $C_1$–$C_{20}$ alkyl, $C_1$–$C_{20}$ alkoxyl, $C_6$–$C_{20}$-aryl, $C_7$–$C_{20}$ alkylaryl, $C_7$–$C_{20}$ arylalkyl, $C_1$–$C_{20}$ acyloxyl group, optionally containing a silicon atom, or $R^b$ is the bridging divalent group R".

23. A metallocene according to claim 20, wherein Y contains at least two heteroatoms.

24. A metallocene according to claim 20, wherein i is 1, j is 1, and Z has the same meaning as Y.

25. A metallocene according to claim 20, wherein i is 1, j is 1, and Z is a cycolpentadienyl containing group, an open-pentadienyl containing group, a nitrogen containing group, a phosphorus containing group, an oxygen containing group, or a sulfur containing group.

26. A metallocene according to claim 20, wherein group Z is an open-pentadienyl containing group and it comprises a radical of formula (V):

where:

G is a carbon atom, a nitrogen atom, a silicon atom, or a phosphorus atom;

L is a $CR^3R^{3'}$ radical, a $SiR^3R^{3'}$ radical, a $NR^{3''}$ radical, a $PR^{3''}$ radical, an oxygen atom, or a sulfur atom;

L' is a $CR^4R^{4'}$ radical, a Si $R^4R^{4'}$ radical, a $NR^{4''}$ radical, a $PR^{4''}$ radical, an oxygen atom, or a sulfur atom;

$R^2$, $R^3$, $R^{3'}$, $R^{3''}$, $R^4$, $R^{4'}$, $R^{4''}$, and $R^5$, are the same or different from each other, can be hydrogen, a linear or branched $C_1$–$C_{20}$ hydrocarbon radical, a linear or branched, $C_1$–$C_{20}$ halocarbon radical, a $C_1$–$C_{20}$ hydrohalocarbon radical, a $C_1$–$C_{20}$ alkoxy radical, a $C_3$–$C_{12}$ cyclohydrocarbon radical, a $C_3$–$C_{12}$ cyclohydrohalocarbon radical, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical, or a halogen atom; $R^2$ and $R^3$, $R^{3'}$ or $R^{3''}$ and/or $R^5$ and $R^4$, $R^{4'}$ or $R^{4''}$ can form together a 4 to 6 membered ring or a 6 to 20 fused ring system; $R^3$, $R^{3'}$, or $R^{3''}$ and $R^4$, $R^{4'}$, or $R^{4''}$ can be joined together so that the five numbered atomic centers of the six π electron central radical are part of a 7 to 20 membered ring system.

27. A metallocene according to claim 20, wherein i is 1, j is 1, and ii is 1, and at least one β substituent on either Y or Z is a bulky group sterically larger than hydrogen or a fluorine atom.

28. A metallocene according to claim 20, wherein i is 1, j is 1, and where both Y and Z are bilaterally or pseudo-bilaterally symmetric and where Y or Z has at least one β substituent larger than hydrogen.

29. A metallocene according to claim 20, wherein i is 1, j is 1, and where one or both Y and Z are not bilaterally or pseudo-bilaterally symmetric, Y or Z having at least one β substituent larger than hydrogen.

30. A metallocene according to claim 29, having Cs or pseudo-Cs symmetry.

31. A catalytic system for the polymerization of addition polymerizable monomers, comprising the reaction product between:
   (1) an heterocyclic metallocene as described in claim 20, and
   (2) a suitable co-catalyst selected from the group consisting of trialkylaluminum, trialkyloxyaluminum, dialkylaluminum halides, alkylaluminum halides, and alumoxane.

32. A catalytic system according to claim 31, wherein the co-catalyst is an alumoxane.

33. A process for polymerizing addition polymerizable monomers, comprising contacting at least one catalytic system, as described in claim 31, with at least one addition polymerizable monomer.

34. A process according to claim 33, comprising contacting the metallocene contained in the catalytic system with a suitable co-catalyst, either prior to or after the metallocene is brought into contact with the monomer.

35. A process according to claim 33, comprising the following steps:
   a) contacting the catalytic system with a small amount of the addition polymerizable monomer, to form a pre-polymerized catalyst; and
   b) contacting the pre-polymerized catalyst obtained in step (a) with the addition polymerizable monomers.

36. A process according to claim 33, for the production of polyethylene, isotactic, syndiotactic, hemi-isotactic, atactic polypropylene, polyethylene copolymers, or polypropylene copolymers.

37. A metallocene according to claim 21, wherein Y is represented by the following formulae:

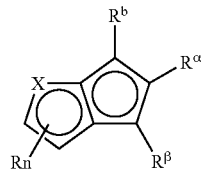
(a)

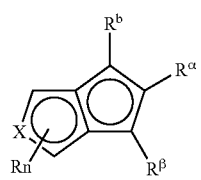
(b)

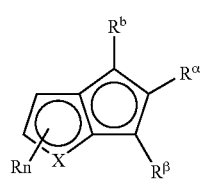
(c)

-continued

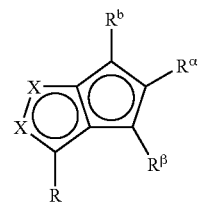
(d)

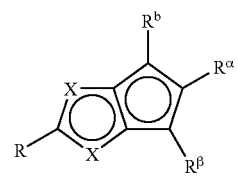
(e)

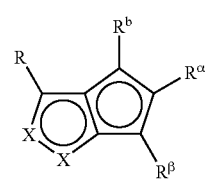
(f)

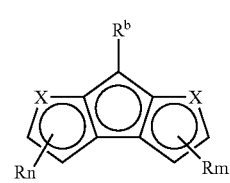
(g)

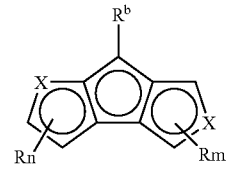
(h)

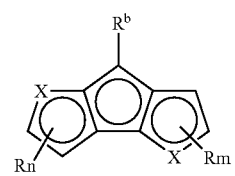
(i)

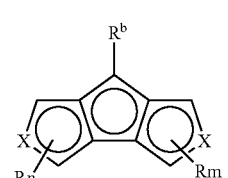
(j)

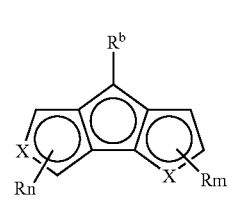
(k)

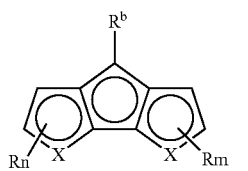 (l)
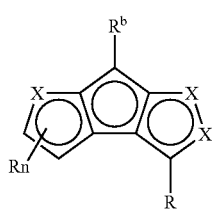 (m)
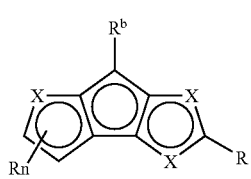 (n)
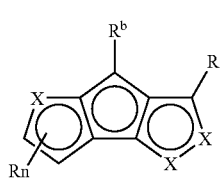 (o)
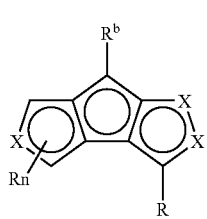 (p)
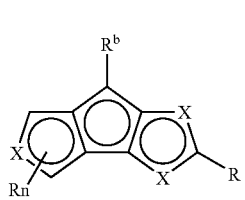 (q)
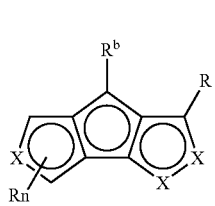 (r)
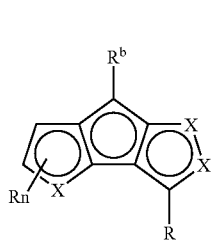 (s)
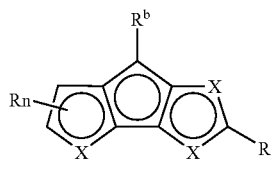 (t)
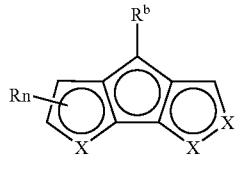 (u)
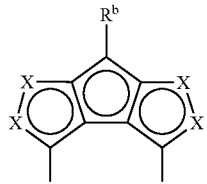 (v)
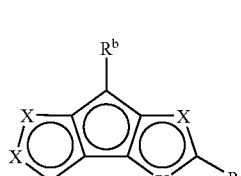 (w)
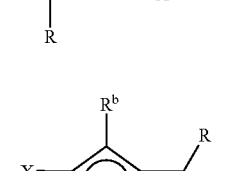 (x)
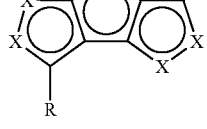 (y)
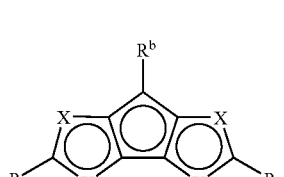 
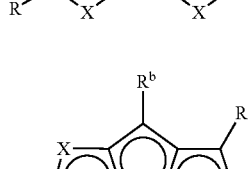 (z)
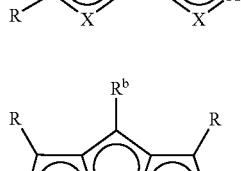 (aa)

-continued

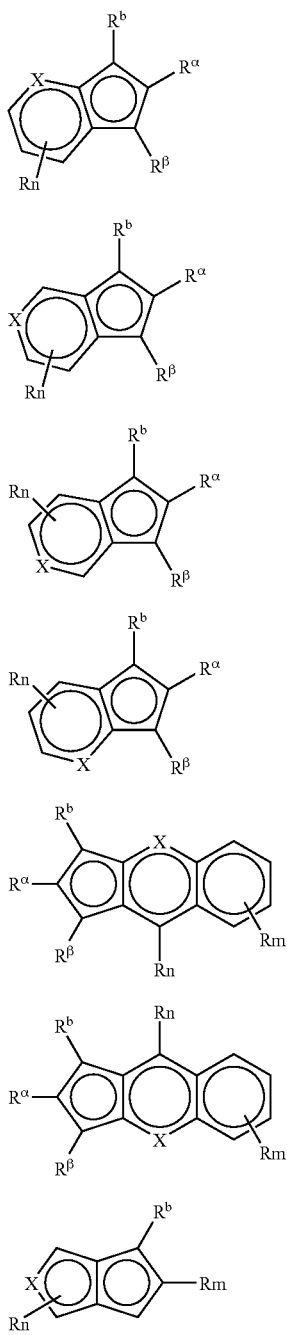

(bb)

(cc)

(dd)

(ee)

(ff)

(gg)

(hh)

wherein:
(i) the X atoms are the same or different from each other, can be N, P, $NR^g$, $PR^g$, O or S; when a fused ring has two heteroatoms, then one X can be O or S the other X can be N, P, $NR^g$ or $PR^g$, or one can be N or P and the other can be $NR^g$ or $PR^g$, so that the molecular species represents a chemically viable group;
(ii) wherein $R^g$ a linear or branched $C_1$–$C_{20}$ hydrocarbon radical, optionally substituted with one or more halogen, hydroxy, alkoxy group, a $C_3$–$C_{12}$ cyclohydrocarbon radical, a $C_3$–$C_{12}$ cyclohydrohalocarbon radical, optionally substituted with one or more halogen, $C_6$–$C_{20}$ aryl radical, $C_7$–$C_{20}$ alkylaryl radical, $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical or a halogen atom;

(iii) the R groups, the same or different from each other, can be hydrogen, a linear or branched $C_1$–$C_{20}$ hydrocarbon radical, optionally substituted with one or more halogen, hydroxy, alkoxy, a $C_3$–$C_{12}$ cyclohydrohalocarbon radical, optionally substituted with one or more halogen, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical, or a halogen atom, two adjacent R groups can form together a saturated, unsaturated, or aromatic fused ring;

(iv) n and m are integers which have values from 0 to the maximum number of substituents that the ring can accommodate;

(v) $R^\alpha$ and $R^\beta$ representing $\alpha$ and $\beta$ substituents respectively, are the same or different from each other, can be hydrogen, a linear or branched $C_1$–$C_{20}$ hydrocarbon radical, optionally substituted with one or more halogen, hydroxy, or alkoxy, a $C_3$–$C_{20}$ cyclohydrocarbon radical, optionally substituted with one or more halogens, a $C_6$–$C_{20}$ aryl radical, a $C_7$–$C_{20}$ alkylaryl radical, a $C_7$–$C_{20}$ arylalkyl radical, a silicon hydrocarbon radical, a germanium hydrocarbon radical, a phosphorous hydrocarbon radical, a nitrogen hydrocarbon radical, a boron hydrocarbon radical, an aluminum hydrocarbon radical, or a halogen atom; two adjacent $R^\alpha$ and $R^\beta$ groups can form together a saturated, unsaturated, or aromatic fused ring; and (vi) $R^b$ is a hydrogen, halogen, linear or branched, saturated or unsaturated, $C_1$–$C_{20}$ alkyl, $C_1$–$C_{20}$ alkoxyl, $C_6$–$C_{20}$ aryl, $C_7$–$C_{20}$ alkylaryl, $C_7$–$C_{20}$ arylalkyl, $C_1$–$C_{20}$ acyloxyl group, optionally containing a silicon atom, or $R^b$ is the bridging divalent group R".

38. A ligand according to claim 12, wherein Y is represented by the following formulae:

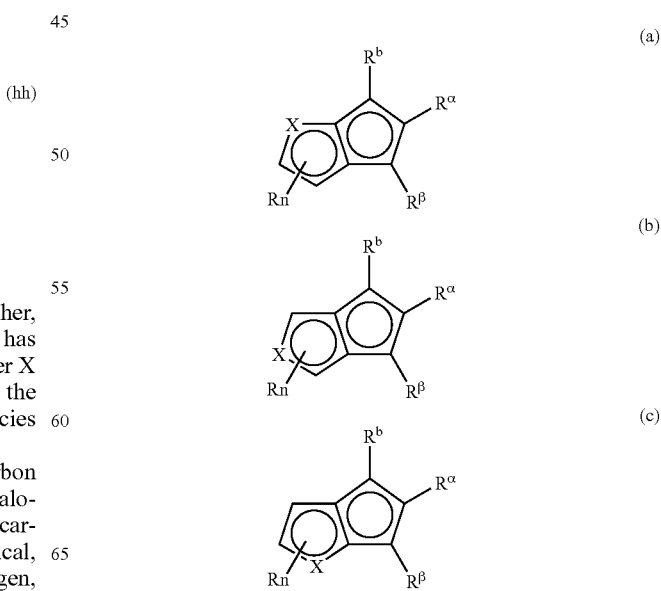

-continued
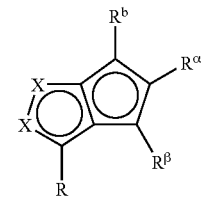
(d)
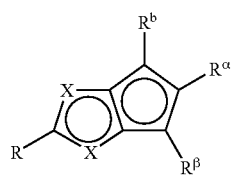
(e)
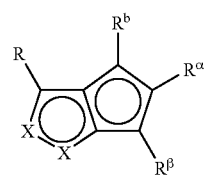
(f)
-continued
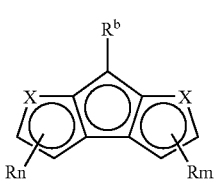
(g)
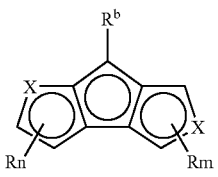
(h)
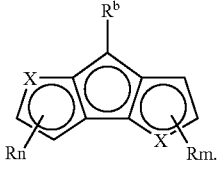
(i)
* * * * *

UNITED STATES PATENT AND TRADEMARK OFFICE
CERTIFICATE OF CORRECTION

PATENT NO. : 7,238,818 B2  Page 1 of 1
APPLICATION NO. : 10/395686
DATED : July 3, 2007
INVENTOR(S) : Ewen et al.

It is certified that error appears in the above-identified patent and that said Letters Patent is hereby corrected as shown below:

Please insert the following new section, including a new heading and paragraph: column 1, line 5

CROSS REFERENCE TO RELATED APPLICATIONS

This application is a continuation of U.S.S.N. 09/308,308, filed May 17, 1999, now abandoned, which, in turn, is a 35 U.S.C. § 371 of PCT Application No. PCT/EP97/06297 filed November 12,1997, which, in turn, is based upon and claims the benefit of European Application No. 96118369.6, filed November 15, 1996.

Signed and Sealed this

Fourteenth Day of April, 2009

JOHN DOLL
*Acting Director of the United States Patent and Trademark Office*